US008389002B2

(12) United States Patent
Shin et al.

(10) Patent No.: US 8,389,002 B2
(45) Date of Patent: Mar. 5, 2013

(54) ANTI-CANCER MEDICINE BOTH FOR DIAGNOSING AND TREATING CANCER

(75) Inventors: Dong-Youn Shin, Seoul (KR); Jang-Seop Kim, Seoul (KR)

(73) Assignee: Youl Chon Chemical Co., Ltd., Seoul (KR)

( * ) Notice: Subject to any disclaimer, the term of this patent is extended or adjusted under 35 U.S.C. 154(b) by 596 days.

(21) Appl. No.: 12/600,977

(22) PCT Filed: Jul. 5, 2007

(86) PCT No.: PCT/KR2007/003271
§ 371 (c)(1),
(2), (4) Date: Nov. 19, 2009

(87) PCT Pub. No.: WO2008/146976
PCT Pub. Date: Dec. 4, 2008

(65) Prior Publication Data
US 2010/0158812 A1    Jun. 24, 2010

(30) Foreign Application Priority Data

May 29, 2007  (KR) .................. 10-2007-0051970
Jul. 4, 2007    (KR) .................. 10-2007-0066909

(51) Int. Cl.
*A61K 9/127*       (2006.01)
(52) U.S. Cl. ......................................... 424/450
(58) Field of Classification Search .................. None
See application file for complete search history.

(56) References Cited

FOREIGN PATENT DOCUMENTS
KR        10-0626767 B1    9/2006
WO    WO 2006/095936 A1   9/2006
WO    WO 2007/007976 A1   1/2007

OTHER PUBLICATIONS

Sahoo et al, Nanotech approaches to drug delivery and imaging, Drug Discovery Today, 2003, 24(8), 1112-1120.*
PCT International Search Report and Written Opinion of the International Searching Authority, PCT/KR2007/003271, Feb. 26, 2008, 7 pages.
Kakizawa, Yoshinori et al., "Block Copolymer Micelles for Delivery of Gene and Related Compounds," Advanced Drug Delivery Reviews, 54 (2002), pp. 203-222.
Sun, Conroy et al., "Folic acid-PEG conjugated superparamagnetic nanoparticles for targeted cellular uptake and detection by MRI," Journal of Biomedical Materials Research, Part A, May 30, 2006, vol. 78A, No. 3, pp. 550-557, ISSN 1549-3296.
European Patent Office, Supplementary European Search Report and Search Opinion, European Patent Application No. 07768617.8, May 3, 2012, five pages.

* cited by examiner

*Primary Examiner* — Paul Dickinson
(74) *Attorney, Agent, or Firm* — Fenwick & West LLP

(57) ABSTRACT

Disclosed is an anti-cancer medicine comprising a chain end functionalized polymer, a contrast material such as iron oxide and a chemotherapeutic agent such as doxorubicin or pharmaceutically acceptable salts thereof. The anti-cancer medicine performs diagnosis and treatment of cancer at the same time, remarkably reduces a cardiotoxic side effect of the doxorubicin and has an excellent targeting function to the cancer part to considerably increase the anti-cancer effect. At the same time, the anti-cancer medicine is provided as MRI contrast medium which can diagnose the cancer and monitor a progress of the disease. In particular, the anti-cancer medicine is disclosed which is superior to the diagnosis and treatment of the solid cancer and can effectively perform the diagnosis and treatment of the metastatic cancer as well as the primary cancer at the same time.

13 Claims, 17 Drawing Sheets a) saline treatment

Before treatment     After treatment b) doxorubicin treatment

Before treatment     After treatment c) polymer micelle type
anti-cancer medicine treatment Before treatment     After treatment a) saline treatment Before treatment     After treatment b) doxorubicin treatment Before treatment     After treatment c) polymer micelle type anti-cancer medicine treatment Before treatment     After treatment

ANTI-CANCER MEDICINE BOTH FOR DIAGNOSING AND TREATING CANCER

TECHNICAL FIELD

The invention relates to polymer micelle type contrast medium and anti-cancer medicine for diagnosing and treating cancer. More particularly, the invention relates to micelle type nano particulate contrast medium and anti-cancer medicine including chemotherapeutic agent, for example contrast material such as chain end functionalized polymer and iron oxide, and doxorubicin or pharmaceutically acceptable salts thereof, which are capable of diagnosing and effectively treating the cancer while reducing side effects.

BACKGROUND ART

In general, the polymer, which is used as a transporter for delivering drug into the organism, needs to be biologically synthesized or to be biodegraded. For example, the polymer such as PLGA is degraded into lactic acid and glycolic acid in the organism, so that it does not have a harmful influence on the organism. Therefore, when the drug transporter is made using the biodegradable polymer, a continuous emission effect can be expected with respect to the various drugs. In particular, for a drug that maintains a constant blood level to exhibit its drug effect only when it is administrated at a predetermined time period, when the drug is encapsulated in the drug transporter made of the biodegradable polymer, the drug is continuously emitted as the polymer carrier is degraded. Accordingly, such sustained releases are applied to the various drugs. The carrier having the emission mechanism includes microsphere, nano-particle, micelle and the like.

The nano-particle is a kind of colloidal non-uniform dispersion particles having a large surface area of a size of several nm to hundreds of nm. As a variety of researches on the preparation, close characteristic examination and drug encapsulation of the nano-particles have been performed, a possibility as the drug transporter thereof has been sufficiently proved. When the nano-particles are introduced into the organism, they are transferred through a variety of methods such as injection, oral administration, skin and the like. At this time, the distributions of the drug are different a little. One of them is a drug transporter using the nano-particles that are colloidal dispersion particles.

The polymer micelle is a promising transporter in a drug delivery system. Typically, the block copolymer micelle, which is comprised of amphoteric block copolymers, has been used as a transporter of hydrophobic drugs such as chemotherapeutic agent (Y. Kazizawa and K. Kataoka, Drug. Del. Rev., 54(2), 203-222 (2002)). A single polymer micelle consists of hundreds of block copolymers and has a diameter of 20~50 nm. The micelle has two circular parts, i.e., a center of the hydrophobic blocks closely packed and a hydrophilic shell part.

A representative example of the chemotherapeutic agent for treating cancer, which has been used up to now, includes doxorubicin or adriamycin, cisplatin, taxol, 5-fluorouracil, which are widely used in a chemical treatment method for treating the cancer. However, even when only a treatable amount of the agent is administrated, a patient feels a severe pain. The reason of the symptom is that the chemotherapeutic agent acts on not only the cancer cells but only the general cells.

In order to solve the problem, when a chemotherapeutic agent is administrated using nano particles, it is specifically transported to the tissue of the cancer cells, in which the cell junction in the inner wall of the blood vessel is relatively loose, and it cannot transmit well the general cells in which the cell junction is dense, because of the size of the specific particles ranging from several nm to hundreds of nm. Accordingly, if the chemotherapeutic agent is administrated using such principle, the non-specificity of the chemotherapeutic agent can be physically overcome.

In the mean time, one of the problems of the drug transporters, which include the chemotherapeutic agent as the drug, is that the chemotherapeutic agent used is not continuously emitted. In other words, in the case of the conventional drug transporters, the chemotherapeutic agent on the surfaces of the carriers is emitted in the form of diffusion at the early stage, so that the emission at the early stage is considerably high. However, as time goes by, the emission is gradually decreased, so that it is difficult to maintain a constant blood level.

In addition, the large amount of the chemotherapeutic agent should be encapsulated in the transporters. The large amount of the chemotherapeutic agent is used, so that the lost ratio is high in the formulation process of the drug transporter using the chemotherapeutic agent or in the other compounding processes. In this regard, it has been already reported that 50% or more of the chemotherapeutic agent in the transporter is lost after preparing the transporters. Therefore, many researchers put their hearts and souls into the efforts for increasing the encapsulating ratio of the chemotherapeutic agent used as the drug.

DISCLOSURE

Technical Problem

An object of the invention is to solve to the above problems occurring in the prior art.

Another object of the invention is to diagnose and to treat the cancer at the same time.

Still another object of the invention is to remarkably increase effects of the conventional anti-cancer chemotherapeutic agent.

Yet still another object of the invention is to considerably decrease the side effects of the conventional anti-cancer chemotherapeutic agent. Another object of the invention is to remarkably decrease the cardiotoxic side effect of the doxorubicin.

Another object of the invention is to specifically transfer the doxorubicin to a cancer region only.

Another object of the invention is to diagnose and to treat the solid cancer at the same time.

Another object of the invention is to diagnose and to treat the metastatic cancer as well as the primary cancer at the same time.

Another object of the invention is to provide anti-cancer medicine having an excellent solubility and a stable formulation and exhibiting a small side effect when it is administrated to patients.

Another object of the invention is to transfer anti-cancer medicine and to serve as a contrast medium, thereby diagnosing a disease and monitoring the progress of the disease.

Another object of the invention is provide anti-cancer medicine in a form of a nano-particle, thereby obtaining a targeting effect of specifically transferring the anti-cancer medicine to a tissue of cancer cells in which the cell junction in the inner wall of the blood vessel is relatively loose. In addition, an object of the invention is to reduce an amount of the anti-cancer medicine used due to the high targeting effect.

Another object of the invention is to enable a chemotherapeutic agent to be gradually emitted, thereby maintaining an efficacy of the anti-cancer medicine and preventing the side effects of the anti-cancer medicine.

Another object of the invention is obtain an excellent anti-cancer effect and to decrease the side effects with an amount equal to or less than a dosage of the conventional anti-cancer medicine.

Technical Solution

In order to achieve the above objects, there is provided an anti-cancer medicine performing diagnosis and treatment of cancer at the same time and comprising:

a chain end functionalized polymer expressed as a following chemical formula 1;

[chemical formula 1]

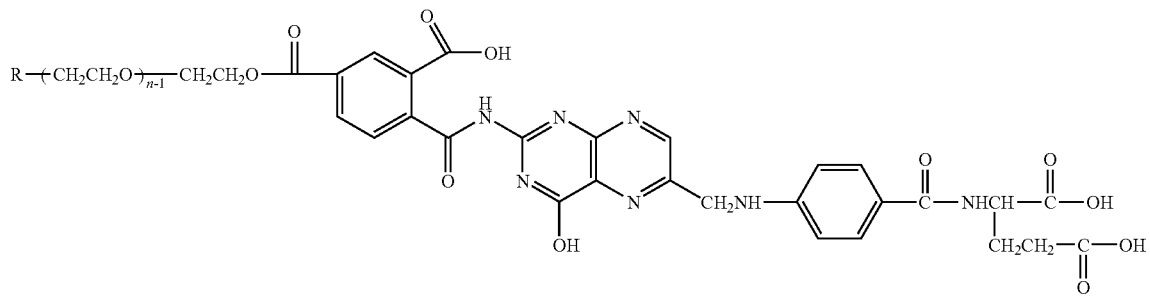

wherein, R is methyl, n-butyl, sec-butyl, tert-butyl or methoxy and n is an integer of 10 to 500, a contrast material; and a chemotherapeutic agent, wherein the anti-cancer medicine is in a form of a nano-particle having a micelle structure.

In addition, according to another embodiment of the invention, there is provided a polymer micelle type contrast medium performing diagnosis of cancer and comprising:

a polymer expressed as a following chemical formula 1;

In the mean time, according to another aspect of the invention, there is provided a method of preparing a polymer micelle type anti-cancer medicine comprising: a first step of dissolving drug in dimethylsulfoxide (DMSO) to prepare a DMSO solution of the drug; a second step of adding triethylamine to the solution obtained; a third step of dissolving a chain end functionalized polymer in the DMSO to prepare a DMSO solution of the polymer; a fourth step of mixing the DMSO solution of the drug and the DMSO solution of the polymer; a fifth step of adding a contrast material to the solution obtained; and a sixth step of dialyzing and lyophilizing the solution obtained.

In addition, according to another embodiment of the invention, there is provided a method of preparing a polymer micelle type contrast medium comprising: a first step of dissolving a chain end functionalized polymer in DMSO to prepare a DMSO solution of the polymer; a second step of adding a contrast material to the polymer solution obtained; and a third step of dialyzing and lyophilizing the solution obtained.

Advantageous Effects

The polymer micelle type anti-cancer medicine of the invention can treat the cancer and serve as a contrast medium, thereby diagnosing the cancer and monitoring a progress of the disease. In addition, the polymer micelle type anti-cancer (chemical formula 1)

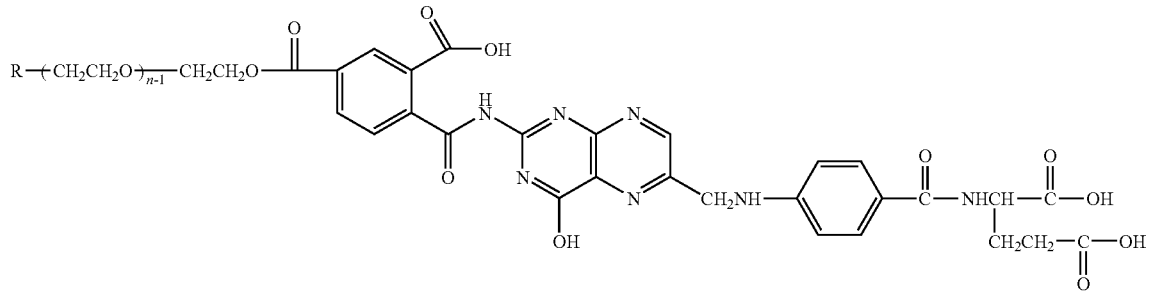

wherein, R is methyl, n-butyl, sec-butyl, tert-butyl or methoxy, and n is an integer of 10 to 500, and a contrast material, wherein the contrast medium is in a form of a nano-particle having a micelle structure.

medicine of the invention can remarkably decrease the cardiotoxic side effect of the doxorubicin. The invention provides the anti-cancer medicine in a form of the nano-particle, thereby exhibiting a targeting effect of specifically transferring the anti-cancer medicine to a tissue of the cancer cells, in which the cell junction in the inner wall of the blood vessel is relatively loose. In addition, due to the high targeting effect, it is possible to decrease an amount of the anti-cancer medicine used and to remarkably decrease the side effects and toxicity. Furthermore, when the anti-cancer medicine is used as an amount equal to the prior art, the higher anti-cancer effect can be obtained due to the targeting effect. The polymer micelle type anti-cancer medicine of the invention is enabled to be gradually emitted, so that the efficacy of the drug can be maintained for a long time and a side effect due to the temporary great emission can be also prevented. In addition, the polymer micelle type anti-cancer medicine of the invention has an excellent solubility and a stable formulation and exhibits a small side effect when it is administrated to patients.

DESCRIPTION OF DRAWINGS

The above and other objects, features and advantages of the present invention will be more apparent from the following detailed description taken in conjunction with the accompanying drawings, in which.

BEST MODE

Figure 1:
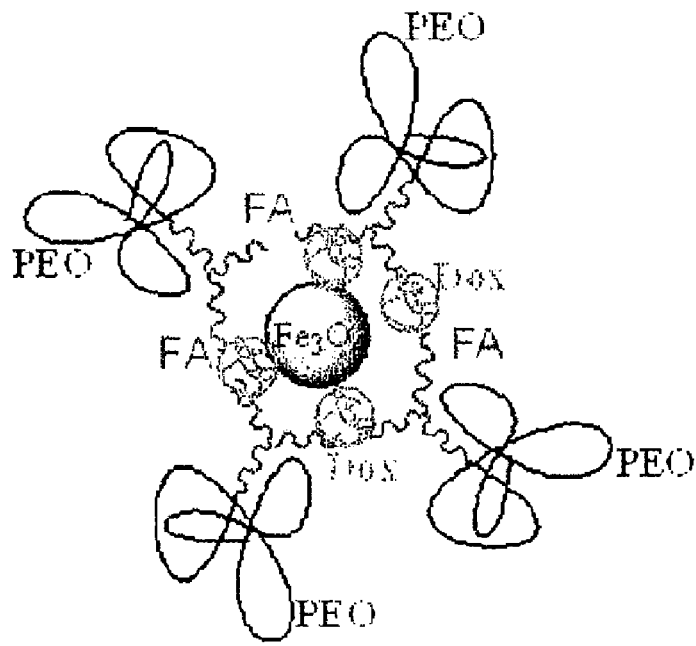
FIG. 1 shows a structure of polymer micelle type anti-cancer medicine according to an embodiment of the invention.

Hereinafter, the invention will be more specifically described.

In an embodiment of the invention, the polymer of the chemical formula 1 may be a chain end functionalized polyethylene oxide. In another embodiment of the invention, the polymer of the chemical formula 1 may be a chain end functionalized methoxy polyethylene glycol (m-PEG). Specifically, when R in the chemical formula 1 is methyl, n-butyl, sec-butyl or tert-butyl, the polymer is a chain end functionalized polyethylene oxide. In the mean time, when R in the chemical formula 1 is methoxy, the polymer is a chain end functionalized methoxy polyethylene glycol (m-PEG).

When n in the chemical formula 1 is less than 10, it is difficult to form a micelle as a polymer. When n is larger than 500, the size of the micelle particle is so large, so that it is difficult to targetingly transfer the micelle to a desired cancer cell only.

In an embodiment of the invention, the chain end functionalized polymer has preferably a number-average molecular weight of 1,100~23,000. When the molecular weight is less than 1,100, it is difficult to form a micelle as a polymer. When the molecular weight is larger than 23,000 the size of the micelle particle is so large, so that it is difficult to targetingly transfer the micelle to a desired cancer cell only.

A composition of the anti-cancer medicine according to an embodiment of the invention has a weight ratio of the chain end functionalized polymer:the iron oxide:the doxorubicin or pharmaceutically acceptable salts thereof of 5~50:2.5~20:1~2. When the iron oxide deviates from the range, the micelle nano-particle is not formed. When an amount of the doxorubicin is too small, an encapsulation ratio is low and when an amount of the doxorubicin is too much, the micelle nano-particle is not formed. When an amount of the polymer is too small, it is difficult to form a micelle structure and when an amount of the polymer is too much, the encapsulation ratio of the doxorubicin or pharmaceutically acceptable salt thereof and the iron oxide is lowered. The amount of the doxorubicin or pharmaceutically acceptable salt thereof means an appropriate ratio that it can be encapsulated in the micelle nano-particle of the invention.

A size of the micelle nano-particle is 30~200 nm, preferably 50~100 nm.

In a polymer micelle type contrast medium composition according to an embodiment of the invention, a contrast material may be selected from iron oxide, gadolinium, manganese, aluminum, silicon, barium, yttrium and rare earth elements, and is preferably iron oxide. The iron oxide ($Fe_3O_4$) helps the cells to be attached to each other, to move and to grow, in particular plays a primary role in the MRI contrast effect and the micelle formation. The iron oxide is preferably a nano-particle.

In the polymer micelle type anti-cancer medicine composition according to an embodiment of the invention, the chemotherapeutic agent encapsulated as drug may be selected from doxorubicin or adriamycin, cisplatin, taxol, 5-fluorouracil and pharmaceutically acceptable salts thereof, and is preferably doxorubicin.

The pharmaceutically acceptable salts of the doxorubicin, which is the chemotherapeutic agent that can be used in the anti-cancer medicine according to an embodiment of the invention, include acid addition salts or base addition salts. An example of the pharmaceutically acceptable base addition salts includes sodium, potassium, calcium, ammonium, organic amino, or magnesium salts or similar salts. An example of the pharmaceutically acceptable acid addition salts include salts derived from inorganic acids such as hydrochloric acid, hydrobromic acid, nitric acid, carbonic acid, dibasic carbonate, phosphate, dibasic phosphate, dihydrogen phosphate, sulfuric acid, dibasic sulfate, hydroiodic acid or phosphorous acid, and salts derived from relatively non-toxic organic acids such as acetic acid, ascorbic acid, propionic acid, isobutyric acid, maleic acid, malonic acid, lactic acid, malic acid, glutamic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, lactobionic acid and the like. In addition, salts of amino acid such as alginate, salts of organic acids such as glucuronic acid or galacturoric acid are also included. Among them, hydrochloric acid salt is preferable.

In the polymer micelle type anti-cancer medicine according to an embodiment of the invention, the cancer is preferably solid tumor.

In the polymer micelle type anti-cancer medicine according to an embodiment of the invention, the cancer may be primary cancer or metastatic cancer.

FIG. 1 shows a structure of the polymer micelle type anti-cancer medicine according to an embodiment of the invention. Here, the contrast material is iron oxide ($Fe_3O_4$), the drug is the doxorubicin that is the chemotherapeutic agent, or pharmaceutically acceptable salt (Dox) thereof. It shows that the polyethylene oxide (PEO) or methoxy polyethylene glycol (m-PEG) having folic acid connected to a chain end forms a micelle structure and the iron oxide and doxorubicin are encapsulated therein.

The doxorubicin or pharmaceutically acceptable salt thereof is intravenous drug that is used so as to treat the solid tumor, and is widely used so as to treat a variety of cancers such as breast, lung, ovarian cancers, hematologic malignancy and the like. The iron oxide helps the cells to be attached to each other, to move and to grow. When the cells are attached to the iron oxide, the cancer cells eat the doxorubicin and the anti-cancer medicine goes to the cancer cells only, without going to the other normal parts. The doxorubicin has the very high anti-cancer effect. However, when the doxorubicin is actually administrated to the patient, the dosage thereof that the patient can endure is very restrictive due to the side effects thereof. When the doxorubicin is administrated too much, it highly damages the normal heart cells, so that the cardiac crisis may be caused. Such side effects can be reduced by the targeting transfer of the drug and the slow emission of the drug.

In the anti-cancer medicine of the invention, the micelle structure is spontaneously formed on the aqueous solution. In addition, the anti-cancer medicine has a characteristic that the drug is gradually emitted depending on the degradation rate of the biodegradable polymer.

In the mean time, the pharmacokinetics of the polymer micelle type anti-cancer in the organism, which is prepared by the invention, is as follows. The micelle structure avoids the renal exclusion and increases the vascular permeability of the drug into the target part by passive diffusion. Furthermore, the drug intake of the micelle structure in the organism is increased due to the increase of the endocytosis and decrease of the multi-drug resistance (MDR) effect. In addition, as the PEO skeleton or mPEG bonded to the drug is chemically degraded, the drug is gradually emitted on the drug-PEO polymer or drug-mPEG polymer fraction.

The polymer micelle type anti-cancer medicine of the invention functions as an effective ingredient of the pharmaceutical formulation and can constitute a pharmaceutical formulation together with the pharmaceutically acceptable carrier, diluent or excipient. At this time, a content of the polymer micelle type anti-cancer medicine of the invention, which is the effective ingredient, is preferably 0.001~99 wt % for the total composition. The useable carrier, excipient or diluent includes lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinyl pyrrolidone, water, methyl hydroxy benzoate, propyl hydroxy benzoate, talc, magnesium stearate and mineral oil and one or more thereof may be used. In addition, when the anti-cancer composition is prepared as drug, it may further include filling agent, anti-aggregatory agent, lubricant, wetting agent, flavor, emulsifier or antiseptic and the like.

The polymer micelle type anti-cancer medicine according to the invention can be administrated in oral, parenteral, rectal, local, percutaneous, intravenous, intramuscular, intraabdominal and subcutaneous administration manners. However, the most preferred administration route is the intravenous administration.

In addition, a dosage of the polymer micelle type anti-cancer medicine according to the invention may be different depending on ages, sexes, weights, specific diseases to be treated or pathological state and severity degrees of a disease or pathological state of patients, administration routes and judgments of the prescriber. A one skilled in the art can determine a dosage based on the above factors. In general, the dosage of the doxorubicin or pharmaceutically acceptable salts thereof is within a range of 1.2~2.4 mg/kg/day. The polymer micelle type anti-cancer medicine according to the invention can be targetingly transferred. Accordingly, the efficacy would be higher when it is administrated in an amount that is typically administrated. In addition, even when the medicine is administrated in an amount less than an amount that is typically administrated, the targeting transfer can be made, so that the effect is similar to a case where it is administrated in a typical amount. Therefore, it is possible to remarkably reduce a dosage of the anti-cancer medicine of the invention.

MODE FOR INVENTION

Hereinafter, the invention will be more specifically described with reference to a preferred embodiment. A one skilled in the art can easily understand that the embodiment is provided to illustrate the invention, not to limit the invention.

Embodiments

PREPARATION EXAMPLE 1

Preparation of PEO-TMA-FA (Polyethylene Oxide-Tritrimellicticanhydride-Folic Acid) Polymer The PEO-TMA-FA of a chemical formula 2 was prepared according to a following method.

[chemical formula 2]

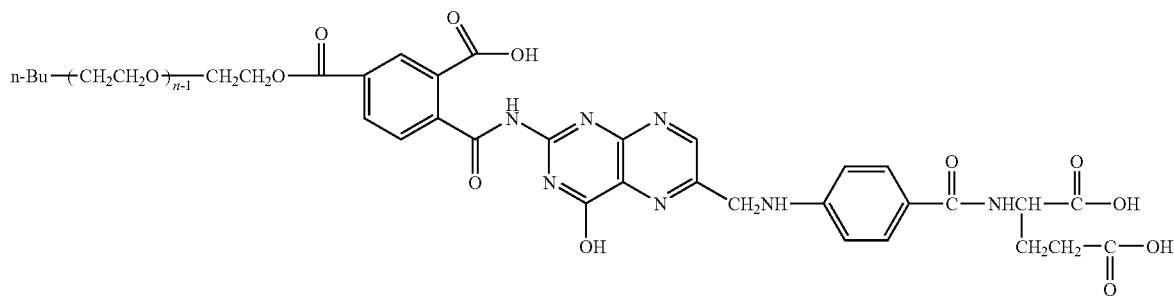

(1) Polymerization of PEO
First, PEO was polymerized as expressed in a reaction 1.

[reaction 1]

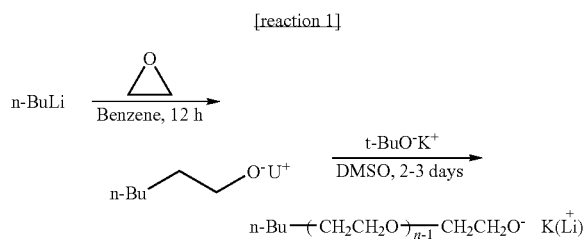

As shown in the reaction 1, various reactants were put in a circular pyrex flask having a capacity of 1 L under high vacuum. Then, the flask was attached to a vacuum line so as to completely remove the air. n-butyllithium (12 mmol) was injected therein under Ar flow with a syringe. A temperature of the reactor was lowered to −78° C. using a dry ice/isopropanol bath, rather than a water bath, and the Ar gas in the reactor was completely removed with a vacuum pump. Again, refined benzene 300 mL was distilled, which was then injected into the reactor. The temperature of the reactor was gradually increased to the room temperature to completely dissolve and reduce the benzene in the reactor into the solution including the initiator. 30 mL (26.5 g) of ethylene oxide (EO) (30 vol %, dilute solution), which was refined at 0° C. using an ice water bath while paying attention to, was introduced into the reactor by breaking up a breakseal. After about 1 hour, t-BuOK (12 mmol in THF 20 mL) and 30 mL of refined DMSO were put into the reactor through the breakseal and stopcock. The temperature of the reactor was increased to 35° C. using the ice water bath and the stirring was performed for 5 hours for reaction. Again, the ice water bath was used to reduce the temperature to 5° C. and the polymerization was performed for 10 minutes. The above procedures were repeated several times. Again, after the reaction for 48 hours at room temperatures, a part of the reactants was taken from the main reactor using an ample and then distilled under reduced pressure to remove the solvent. Then, the remnant was dissolved in the THF, which was then allowed to be deposited in the diethylether. As a result, polyethylene oxide (PEO) was obtained. It was dried in a vacuum oven for 48 hours at the room temperature. Then, it was analyzed with 1H-NMR and gel permeation chromatography (GPC). As a result, an number-average molecular weight of the obtained polymer was 4,400 g/mol. A conversion ratio of EO into the polymer was 100 mol % or more.

(2) Synthesis of PEO-TMA
According to a following reaction 2, PEO-TMA was synthesized and PEO-TMA-FA was again synthesized.

[reaction 2]

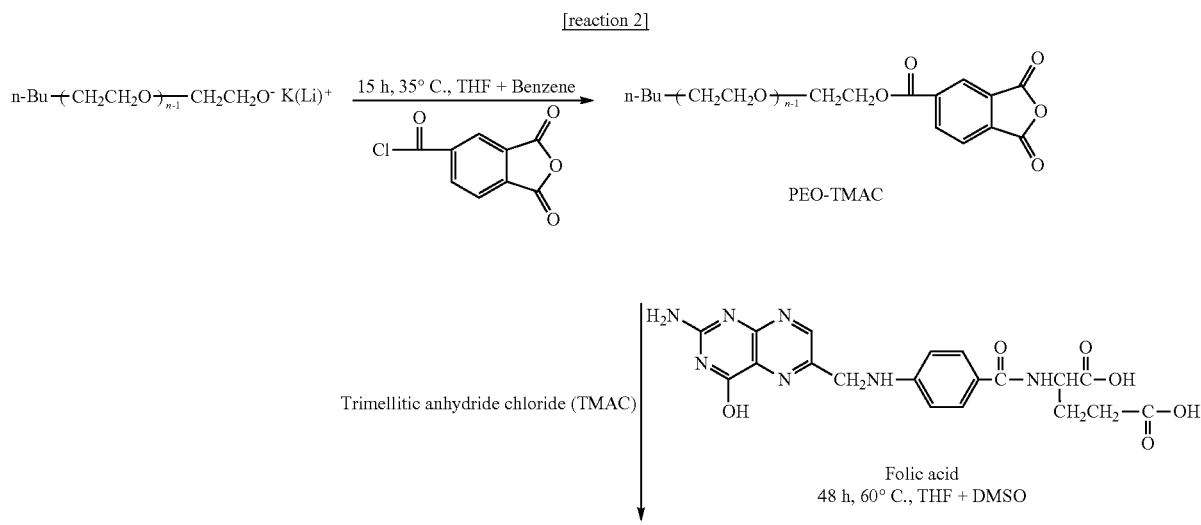

-continued

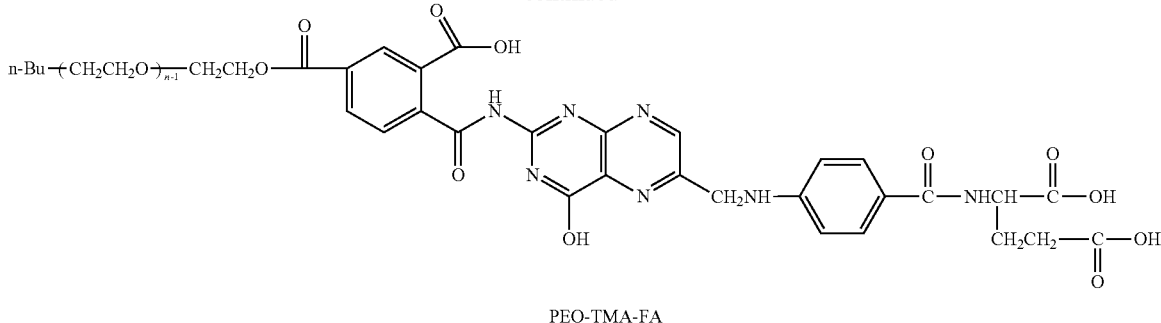

PEO-TMA-FA

As shown in the reaction 2, 0.005 mol of trimellitic anhydride chloride (98%) (Aldrich), which was not refined, was introduced, under high vacuum, in the living polymer solution ([ROLi]=0.001 mol) having a molecular weight of 4,400 g/mol, which was prepared in the above (1), in the ample. Again, 60 mL of THF was distilled and then attached to the reactor, which was then put in the reactor using the breakseal. The reactants were reacted at 5° C. for 1 hour and at 35° C. for 15 hours, which were then deposited in the dimethylether to remove the solvent. The deposits were dissolved in the THF and re-crystallized in the ethanol, thereby preparing chain end anhydride polyethylene oxide (w-anhydride (polyethylene oxide)). The functionalization yield was 98 mol % on the basis of the polymer solution concentration which was initially used, and the number-average molecular weight was 4,600 g/mol.

(3) Synthesis of PEO-TMA-FA

Figure 2:
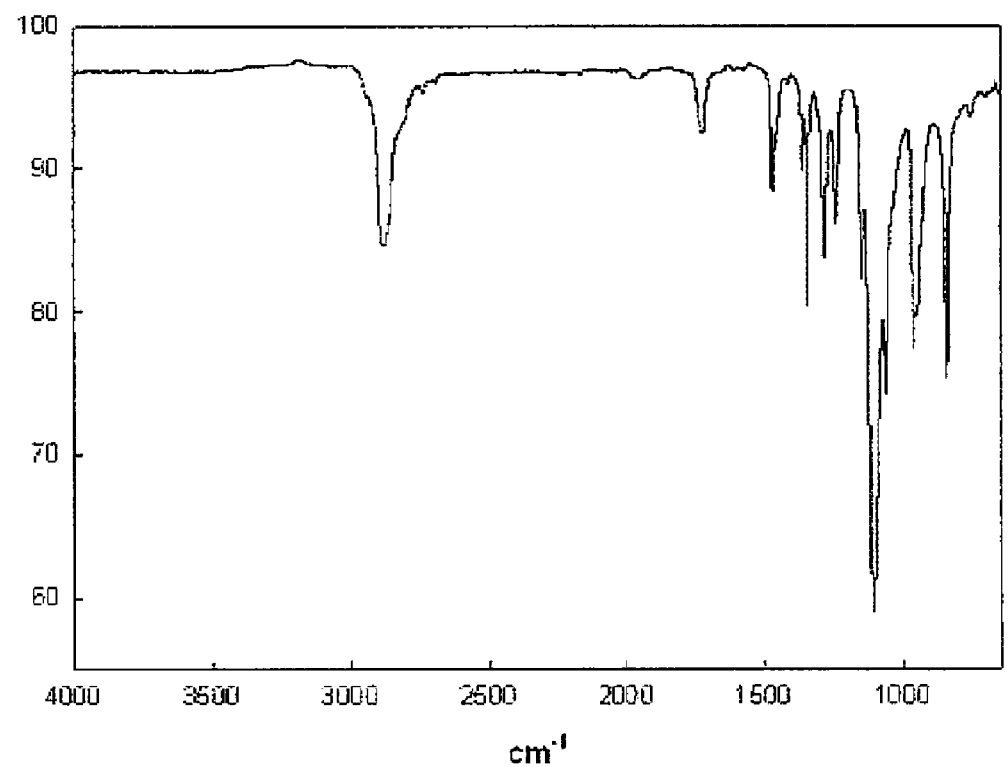
FIG. 2 shows an FT-IR spectrum of a PEO-TMA-FA polymer according to an embodiment of the invention.
Figure 3:
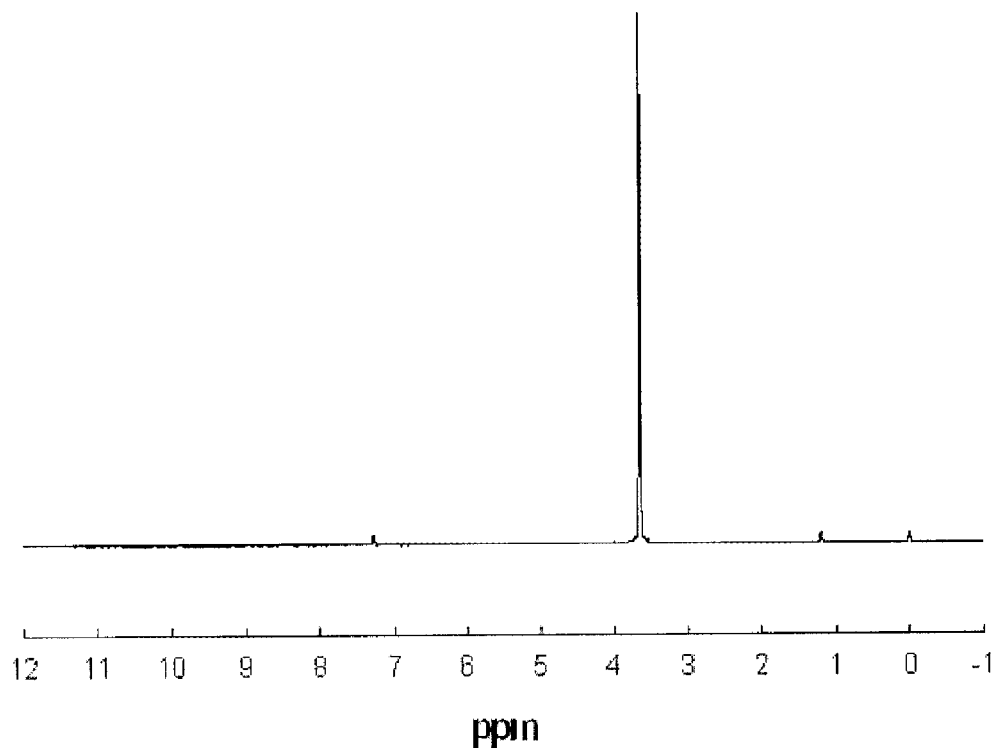
FIG. 3 shows an FT-NMR spectrum of a PEO-TMA-FA polymer according to an embodiment of the invention.
Figure 4:
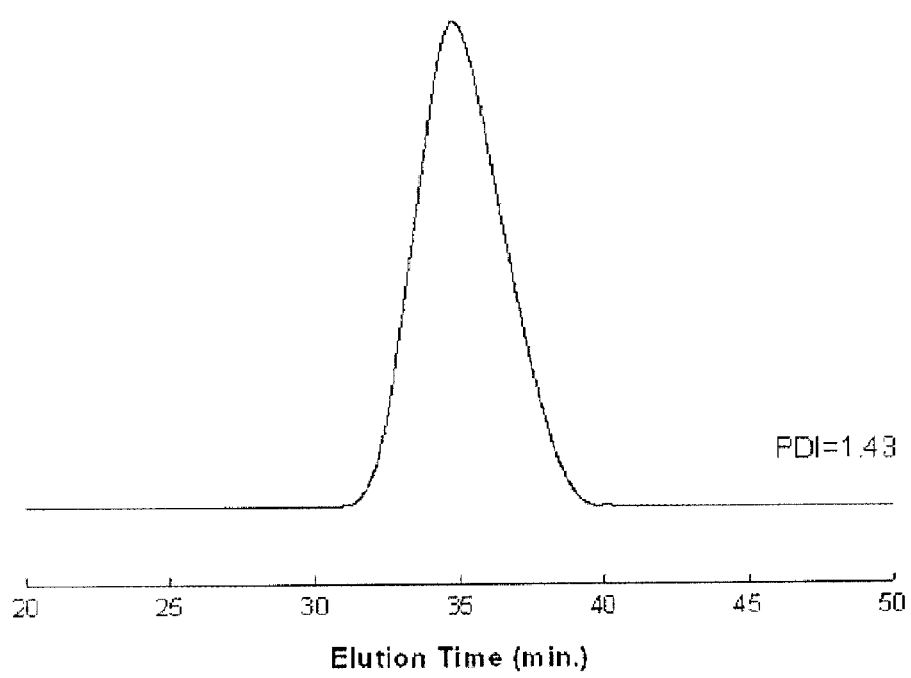
FIG. 4 shows a GPC curve of a PEO-TMA-FA polymer according to an embodiment of the invention.

The w-anhydride-PEO (Mn=4,600 g/mol, 1 g), which was prepared in the above (2), and the folic acid (0.48 g, 5 eq.) were reacted in 20 mL of DMSO at the room temperature for about 24 hours. The mixture was again re-deposited in the diethylether to obtain the solids, which were again dissolved in the THF and re-crystallized in the ethanol to obtain yellow powders (PEO-TMA-FA). The number-average molecular weight was 5,000 g/mol and the reaction yield was 98 mol % or more on the basis of the PEO. The analysis result of the synthesized PEO-TMA-FA compound is shown in FIGS. 2 to 4.

PREPARATION EXAMPLE 2

Preparation of mPEG-TMA-FA (Methoxy Polyethylene Glycol-Trimellitic Anhydride-Folic Acid) Polymer mPEG-TMA-FA expressed by a chemical formula 3 was prepared as follows.

[chemical formula 3]

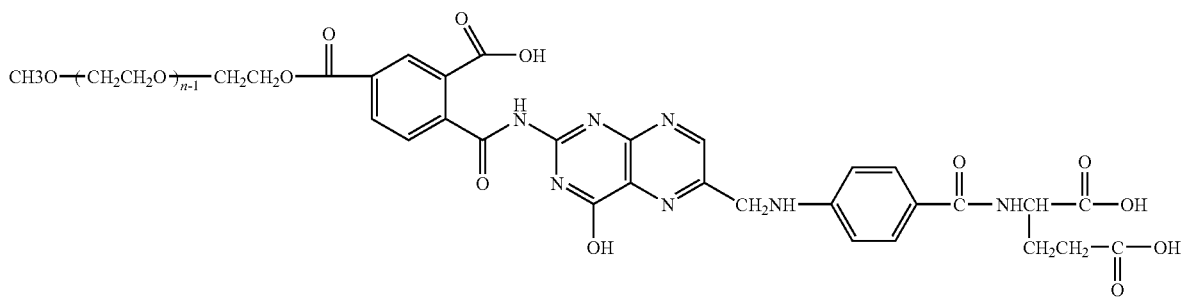

(1) Modification of mPEG
mPEG was modified according to a reaction 3.

[reaction 3]

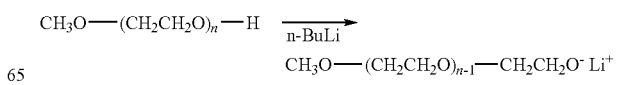

Figure 5:
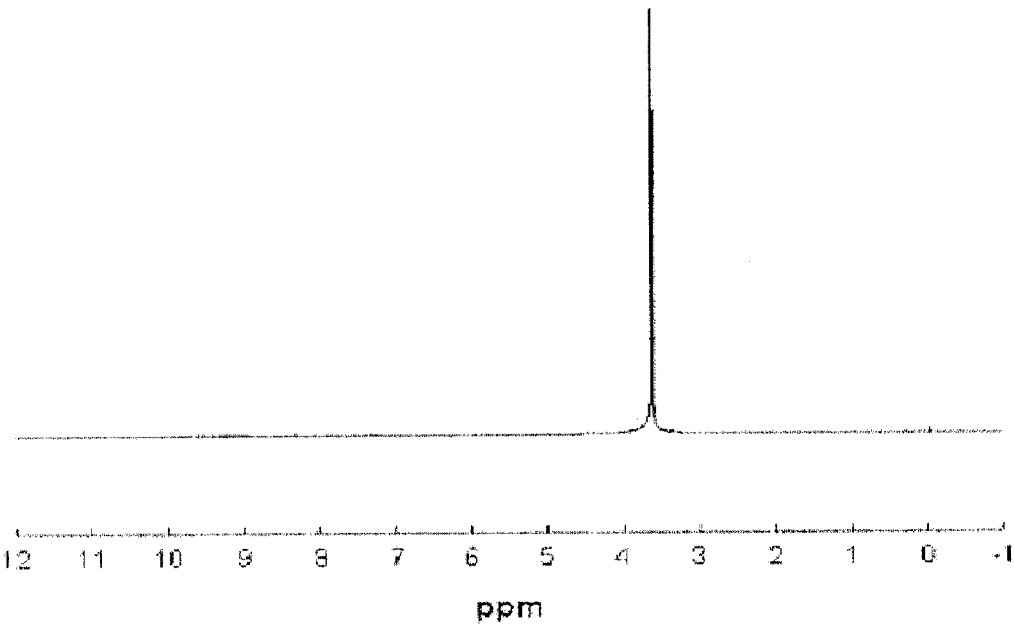
FIG. 5 shows an NMR spectrum of modified mPEG that is prepared according to an embodiment of the invention.
Figure 6:
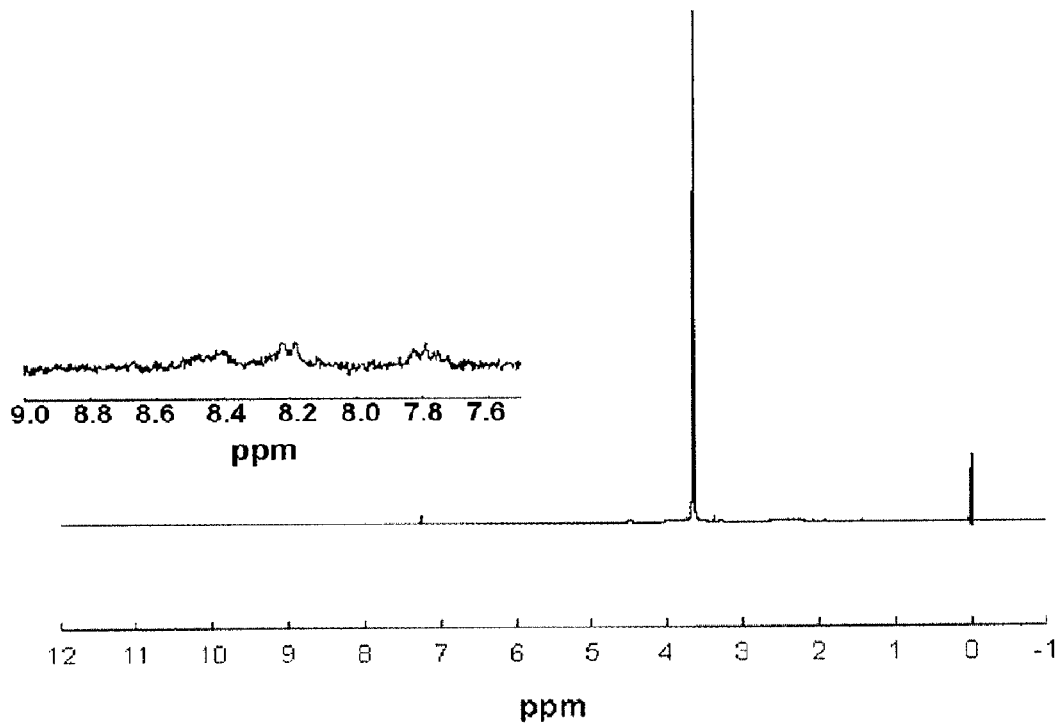
FIG. 6 shows an NMR spectrum of modified mPEG-TMA that is prepared according to an embodiment of the invention.
Figure 7:
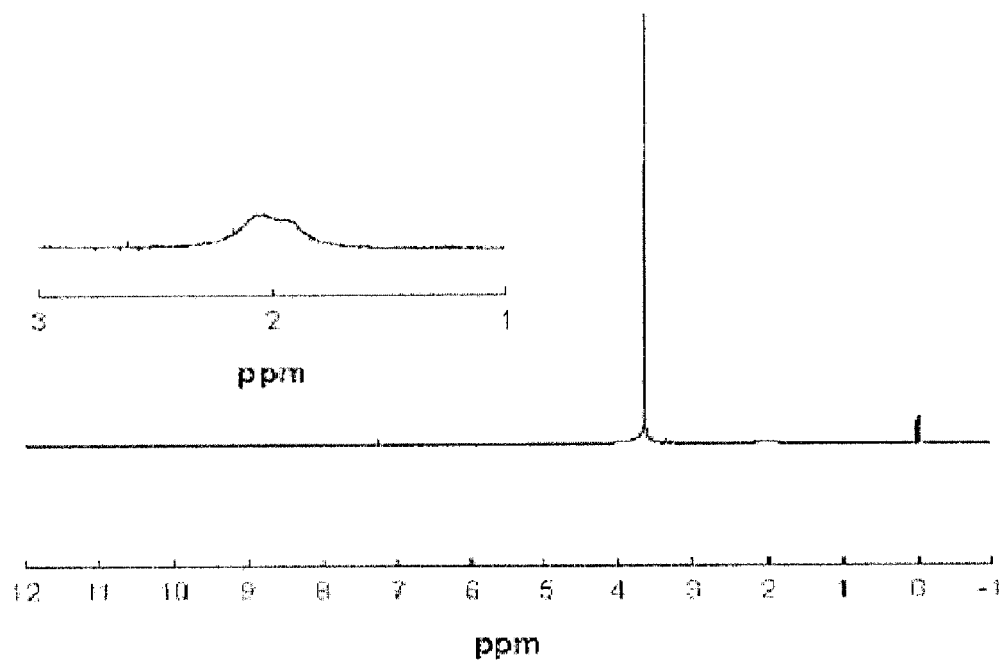
FIG. 7 shows an NMR spectrum of modified mPEG-TMA-TA that is prepared according to an embodiment of the invention.

0.01 mol of methoxy-polyethylene glycol (molecular weight: 5,000 g/mol, Aldrich: mPEG) was put in the round pyrex flask having a capacity of 2 L, which was then inserted in the vacuum line to completely remove the air and was subject to the drying. Benzene 1 L was distilled to dissolve the mPEG, the temperature thereof was decreased using the ice water bath. n-butyllithium (30 mL) was slowly injected therein under Ar flow with a syringe. After the injection, the temperature was slowly increased to 30° C. After the reaction for 48 hours, while checking that the clear color was changed into yellow color, a small amount of methanol was distilled and put in, which was then contacted to the air and the reaction was ended. The resultant was deposited in the diethyl ether to obtain the living methoxy polyethylene glycol (mPEG-Li) in which the end group was replaced with Li. The number-average molecular weight of the polymer obtained was 5,000 g/mol. FIG. 5 shows a NMR spectrum of the modified mPEG obtained.

(2) Synthesis of mPEG-TMA mPEG-TMA-FA was prepared according to a reaction 4.

The trimellitic anhydride chloride (98%) (Aldrich) was dissolved, under Ar air flow, in the THF 60 mL in the living polymer solution ([ROLi]=0.01 mol) having a molecular weight of 5,000 g/mol, which was prepared with the method as in the above (1). Then, it was put into the reactor using a syringe. The reactants were reacted at 5° C. for 1 hour and 35° C. for 15 hours and then deposited in the dimethyl ether to remove the solvent. The deposits were dissolved in the THF and re-crystallized in the ethanol to prepare chain end anhydride polyethylene oxide (ω-anhydride poly(ethylene oxide)). The functionalization yield was 85 mol % on the basis of the polymer solution concentration which was initially used, and the number-average molecular weight was 5,200 g/mol.

(3) Synthesis of mPEG-TMA-FA

The ω-anhydride-mPEG ($M_n$=5,200 g/mol, 1 g), which was prepared in the above (2), and the folic acid (0.42 g, 5 eq.) were reacted in the DMSO at the room temperature for about 24 hours. The mixture was again re-deposited in the diethyl-ether to obtain the solids, which were again dissolved in the THF and re-crystallized in the ethanol to obtain yellow powders (mPEG-TMA-FA). The number-average molecular weight was 5,600 g/mol and the reaction yield was 80 mol % or more on the basis of the mPEG.

Embodiment 1: Preparation of Polymer Micelle Type Contrast Medium Including PEO-TMA-FA 300 mg of polymer (PEO-TMA-FA) having the number-average molecular weight 5,000 g/mol, which was prepared according to the preparation example 1, was put in a 100 mL beaker, into which DMSO 3.5 mL was then put to completely dissolve the polymer. To this solution was put the iron oxide 250 mg (Aldrich, Cat #637106, sphere, particle size: 20~30 nm, purity>98+%) and was added 5% mannitol 10 mL. The beaker was covered with foil and was subject to sonication for 2 hours. Then, the solution was put in a 50 mL conical tube and was subject to a centrifugal separation at 2,000 rpm for 10 minutes. For dialysis, mannitol 1000 g was dissolved in 20 1 DDW to prepare a 5% mannitol solution. At this time, pH thereof was adjusted to be 7.4 with NaOH. Then, the sample for which the centrifugal separation was completely per-

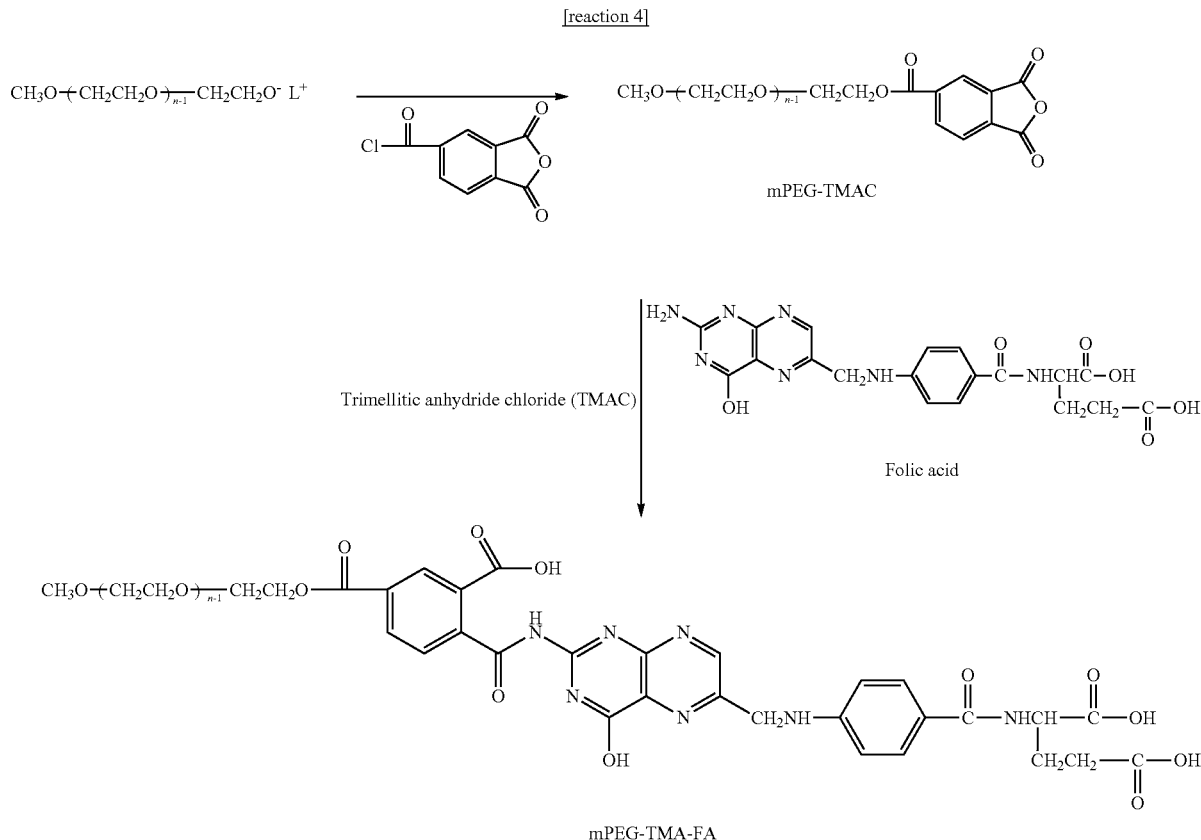

formed was put in a dialysis membrane (MWCO=3,500), which was previously steeped in water. Then, the membrane was bound at its front and rear with a holder, which was then immersed in a dialysis receptacle having solution therein. Then, it was stirred at 500 rpm for 24 hours and was subject to the dialysis while replacing the 5% mannitol solution. The sample for which the dialysis was completely performed was put and frozen in a deep freezer. After that, the sample was lyophilized for 3 days with a freeze-dryer, thereby preparing polymer micelle type contrast medium.

Embodiment 2: Preparation of Polymer Micelle Type Contrast Medium Including PEO-TMA-FA The polymer micelle type contrast medium was prepared with a method same as the embodiment 1, except that 500 mg of the polymer (PEO-TMA-FA) having the number-average molecular weight of 5,000 g/mol was mixed, which was prepared according to the preparation example 1.

Embodiment 3: Preparation of Polymer Micelle Type Contrast Medium Including PEO-TMA-FA The polymer micelle type contrast medium was prepared with a method same as the embodiment 1, except that 600 mg of the polymer (PEO-TMA-FA) having the number-average molecular weight of 5,000 g/mol was mixed, which was prepared according to the preparation example 1.

Embodiment 4: Preparation of Polymer Micelle Type Contrast Medium Including PEO-TMA-FA The polymer micelle type contrast medium was prepared with a method same as the embodiment 1, except that 750 mg of the polymer (PEO-TMA-FA) having the number-average molecular weight of 5,000 g/mol was mixed, which was prepared according to the preparation example 1.

Embodiment 5: Preparation of Polymer Micelle Type Contrast Medium Including PEO-TMA-FA The polymer micelle type contrast medium was prepared with a method same as the embodiment 1, except that 750 mg of the polymer (PEO-TMA-FA) having the number-average molecular weight of 5,000 g/mol, which was prepared according to the preparation example 1, and the iron oxide 50 mg were mixed.

Embodiment 6: Preparation of Polymer Micelle Type Contrast Medium Including PEO-TMA-FA The polymer micelle type contrast medium was prepared with a method same as the embodiment 1, except that 750 mg of the polymer (PEO-TMA-FA) having the number-average molecular weight of 5,000 g/mol, which was prepared according to the preparation example 1, and the iron oxide 100 mg were mixed.

Embodiment 7: Preparation of Polymer Micelle Type Contrast Medium Including PEO-TMA-FA The polymer micelle type contrast medium was prepared with a method same as the embodiment 1, except that 750 mg of the polymer (PEO-TMA-FA) having the number-average molecular weight of 5,000 g/mol, which was prepared according to the preparation example 1, and the iron oxide 150 mg were mixed.

Embodiment 8: Preparation of Polymer Micelle Type Contrast Medium Including PEO-TMA-FA The polymer micelle type contrast medium was prepared with a method same as the embodiment 1, except that 750 mg of the polymer (PEO-TMA-FA) having the number-average molecular weight of 5,000 g/mol, which was prepared according to the preparation example 1, and the iron oxide 200 mg were mixed.

Embodiment 9: Preparation of Polymer Micelle Type Contrast Medium Including PEO-TMA-FA The polymer micelle type contrast medium was prepared with a method same as the embodiment 1, except that 750 mg of the polymer (PEO-TMA-FA) having the number-average molecular weight of 5,000 g/mol, which was prepared according to the preparation example 1, and the iron oxide 225 mg were mixed.

Embodiment 10: Preparation of Polymer Micelle Type Contrast Medium Including PEO-TMA-FA The polymer micelle type contrast medium was prepared with a method same as the embodiment 1, except that 750 mg of the polymer (PEO-TMA-FA) having the number-average molecular weight of 5,000 g/mol, which was prepared according to the preparation example 1, and the iron oxide 250 mg were mixed.

Embodiment 11: Preparation of Polymer Micelle Type Contrast Medium Including PEO-TMA-FA The polymer micelle type contrast medium was prepared with a method same as the embodiment 1, except that 750 mg of the polymer (PEO-TMA-FA) having the number-average molecular weight of 5,000 g/mol, which was prepared according to the preparation example 1, and the iron oxide 275 mg were mixed.

Embodiment 12: Preparation of Polymer Micelle Type Contrast Medium Including mPEG-TMA-FA 300 mg of polymer (mPEG-TMA-FA) having the number-average molecular weight 5,600 g/mol, which was prepared according to the preparation example 2, was put in a 100 mL beaker, into which DMSO 3.5 mL was then put to completely dissolve the polymer. To this solution was put the iron oxide 250 mg and was added 5% mannitol 10 mL. The beaker was covered with foil and was subject to sonication for 2 hours. Then, the solution was put in a 50 mL conical tube and was subject to a centrifugal separation at 2,000 rpm for 10 minutes. For dialysis, mannitol 1000 g was dissolved in 20 l DDW to prepare a 5% mannitol solution. At this time, pH thereof was adjusted to be 7.4 with NaOH. Then, the sample for which the centrifugal separation was completely performed was put in a dialysis membrane (MWCO=3,500), which was previously steeped in water. Then, the membrane was bound at its front and rear with a holder, which was then immersed in a dialysis receptacle having solution therein. Then, it was stirred at 500 rpm for 24 hours and was subject to the dialysis while replacing the 5% mannitol solution. The sample for which the dialysis was completely performed was put and frozen in a deep freezer. After that, the sample was lyophilized for 3 days with a freeze-dryer, thereby preparing polymer micelle type contrast medium.

Embodiment 13: Preparation of Polymer Micelle Type Contrast Medium Including mPEG-TMA-FA The polymer micelle type contrast medium was prepared with a method same as the embodiment 12, except that 500 mg of the polymer (mPEG-TMA-FA) having the number-average molecular weight of 5,600 g/mol was mixed, which was prepared according to the preparation example 2.

Embodiment 14: Preparation of Polymer Micelle Type Contrast Medium Including mPEG-TMA-FA The polymer micelle type contrast medium was prepared with a method same as the embodiment 12, except that 600 mg of the polymer (mPEG-TMA-FA) having the number-average molecular weight of 5,600 g/mol was mixed, which was prepared according to the preparation example 2.

Embodiment 15: Preparation of Polymer Micelle Type Contrast Medium Including mPEG-TMA-FA The polymer micelle type contrast medium was prepared with a method same as the embodiment 12, except that 750 mg of the polymer (mPEG-TMA-FA) having the number-average molecular weight of 5,600 g/mol was mixed, which was prepared according to the preparation example 2.

Embodiment 16: Preparation of Polymer Micelle Type Contrast Medium Including mPEG-TMA-FA The polymer micelle type contrast medium was prepared with a method same as the embodiment 12, except that 750 mg of the polymer (mPEG-TMA-FA) having the number-average molecular weight of 5,600 g/mol, which was prepared according to the preparation example 2, and the iron oxide 50 mg were mixed.

Embodiment 17: Preparation of Polymer Micelle Type Contrast Medium Including mPEG-TMA-FA The polymer micelle type contrast medium was prepared with a method same as the embodiment 12, except that 750 mg of the polymer (mPEG-TMA-FA) having the number-average molecular weight of 5,600 g/mol, which was prepared according to the preparation example 2, and the iron oxide 100 mg were mixed.

Embodiment 18: Preparation of Polymer Micelle Type Contrast Medium Including mPEG-TMA-FA The polymer micelle type contrast medium was prepared with a method same as the embodiment 12, except that 750 mg of the polymer (mPEG-TMA-FA) having the number-average molecular weight of 5,600 g/mol, which was prepared according to the preparation example 2, and the iron oxide 150 mg were mixed.

Embodiment 19: Preparation of Polymer Micelle Type Contrast Medium Including mPEG-TMA-FA The polymer micelle type contrast medium was prepared with a method same as the embodiment 2, except that 750 mg of the polymer (mPEG-TMA-FA) having the number-average molecular weight of 5,600 g/mol, which was prepared according to the preparation example 2, and the iron oxide 200 mg were mixed.

Embodiment 20: Preparation of Polymer Micelle Type Contrast Medium Including mPEG-TMA-FA The polymer micelle type contrast medium was prepared with a method same as the embodiment 12, except that 750 mg of the polymer (mPEG-TMA-FA) having the number-average molecular weight of 5,600 g/mol, which was prepared according to the preparation example 2, and the iron oxide 225 mg were mixed.

Embodiment 21: Preparation of Polymer Micelle Type Contrast Medium Including mPEG-TMA-FA The polymer micelle type contrast medium was prepared with a method same as the embodiment 12, except that 750 mg of the polymer (mPEG-TMA-FA) having the number-average molecular weight of 5,600 g/mol, which was prepared according to the preparation example 2, and the iron oxide 250 mg were mixed.

Embodiment 22: Preparation of Polymer Micelle Type Contrast Medium Including mPEG-TMA-FA The polymer micelle type contrast medium was prepared with a method same as the embodiment 12, except that 750 mg of the polymer (mPEG-TMA-FA) having the number-average molecular weight of 5,600 g/mol, which was prepared according to the preparation example 2, and the iron oxide 275 mg were mixed.

Embodiment 23: Preparation of Polymer Micelle Type Anti-Cancer Medicine Having Contrast Material and Drug Encapsulated in PEO-TMA-FA The doxorubicin hydrochloride 60 mg was put in a 20 mL vial, to which DMSO 1.5 mL was then added to dissolve it. Then, to this solution was put triethylamine (2 eq.), which was then stirred for about 10 minutes. 750 mg of the polymer (PEO-TMA-FA) having the number-average molecular weight 5,000 g/mol, which was prepared according to the preparation example 1, was put in a 100 mL beaker, into which DMSO 3.5 mL was then put to completely dissolve the polymer. To this solution was put the prepared solution containing the doxorubicin, to which the iron oxide 250 mg (Aldrich, Cat #637106, sphere, particle size: 20~30 nm, purity>98+%) and 5% mannitol 10 mL were then added. The beaker was covered with foil and was subject to sonication for 2 hours. Then, the solution was put in a 50 mL conical tube and was subject to a centrifugal separation at 2,000 rpm for 10 minutes, thereby preparing a sample. For dialysis, mannitol 1,000 g was dissolved in 20 l DDW to prepare a 5% mannitol solution. At this time, pH thereof was adjusted to be 7.4 with NaOH. Then, the sample for which the centrifugal separation was completely performed was put in a dialysis membrane (MWCO=3,500), which was previously steeped in water. Then, the membrane was bound at its front and rear with a holder, which was then immersed in a dialysis receptacle having solution therein. Then, it was stirred at 500 rpm for 24 hours and was subject to the dialysis while replacing the 5% mannitol solution. The sample for which the dialysis was completely performed was put and frozen in a deep freezer. After that, the sample was lyophilized for 3 days with a freeze-dryer, thereby preparing polymer micelle type anti-cancer medicine having the doxorubicin encapsulated therein.

Embodiment 24: Preparation of Polymer Micelle Type Anti-Cancer Medicine Having Contrast Material and Drug Encapsulated in PEO-TMA-FA The polymer micelle type antic-cancer medicine was prepared with a method same as the embodiment 23, except that the doxorubicin hydrochloride 70 mg was mixed.

Embodiment 25: Preparation of Polymer Micelle Type Anti-Cancer Medicine Having Contrast Material and Drug Encapsulated in PEO-TMA-FA The polymer micelle type antic-cancer medicine was prepared with a method same as the embodiment 23, except that the doxorubicin hydrochloride 80 mg was mixed.

Embodiment 26: Preparation of Polymer Micelle Type Anti-Cancer Medicine Having Contrast Material and Drug Encapsulated in mPEG-TMA-FA The doxorubicin hydrochloride 60 mg was put in a 20 mL vial, to which DMSO 1.5 mL was then added to dissolve it. Then, to this solution was put triethylamine (2 eq.), which was then stirred for about 10 minutes. 750 mg of the polymer (mPEG-TMA-FA) having the number-average molecular weight 5,600 g/mol, which was prepared according to the preparation example 2, was put in a 100 mL beaker, into which DMSO 3.5 mL was then put to completely dissolve the polymer. To this solution was put the prepared solution containing the doxorubicin, to which the iron oxide 250 mg (Aldrich, Cat #637106, sphere, particle size: 20~30 nm, purity>98+%) and 5% mannitol 10 mL were added. The beaker was covered with foil and was subject to sonication for 2 hours. Then, the solution was put in a 50 mL conical tube and was subject to a centrifugal separation at 2,000 rpm for 10 minutes, thereby preparing a sample. For dialysis, mannitol 1,000 g was dissolved in 20 l DDW to prepare a 5% mannitol solution. At this time, pH thereof was adjusted to be 7.4 with NaOH. Then, the sample for which the centrifugal separation was completely performed was put in a dialysis membrane (MWCO=3,500), which was previously steeped in water. Then, the membrane was bound at its front and rear with a holder, which was then immersed in a dialysis receptacle having solution therein. Then, it was stirred at 500 rpm for 24 hours and was subject to the dialysis while replacing the 5% mannitol solution. The sample for which the dialysis was completely performed was put and frozen in a deep freezer. After that, the sample was lyophilized for 3 days with a freeze-dryer, thereby preparing polymer micelle type anti-cancer medicine having the doxorubicin encapsulated therein.

Embodiment 27: Preparation of Polymer Micelle Type Anti-Cancer Medicine Having Contrast Material and Drug Encapsulated in mPEG-TMA-FA The polymer micelle type antic-cancer medicine was prepared with a method same as the embodiment 26, except that the doxorubicin hydrochloride 70 mg was mixed.

Embodiment 28: Preparation of Polymer Micelle Type Anti-Cancer Medicine Having Contrast Material and Drug Encapsulated in mPEG-TMA-FA The polymer micelle type antic-cancer medicine was prepared with a method same as the embodiment 26, except that the doxorubicin hydrochloride 80 mg was mixed.

COMPARATIVE EXAMPLE 1

The standard doxorubicin (free doxorubicin), which was not subject to the polymer micelle preparation process, was prepared.

EXPERIMENTAL EXAMPLE 1

Measurement of Micelle Structure, Size, Encapsulation Ratio and the Like

First, the sizes of the polymer micelles, which were prepared according to the embodiments 1 to 28, and the encapsulation ratios of the iron oxide and drug are shown in a table 1.

TABLE 1

|  | particle size [Diameter (Wt.)] (nm) | encapsulation ratio of iron oxide (%) | encapsulation ratio of drug (%) |
| --- | --- | --- | --- |
| embodiment 1 | 116.5 (102.1) | 4.5 | — |
| embodiment 2 | 114.0 (101.9) | 4.6 | — |
| embodiment 3 | 115.6 (88.2) | 4.7 | — |
| embodiment 4 | 107.0 (87.4) | 4.7 | — |
| embodiment 5 | 150.7 (199.7) | 3.2 | — |
| embodiment 6 | 125.5 (125.2) | 3.4 | — |
| embodiment 7 | 118.4 (101.4) | 3.4 | — |
| embodiment 8 | 94.8 (67.5) | 4.2 | — |
| embodiment 9 | 100.6 (82.0) | 4.3 | — |
| embodiment 10 | 99.4 (75.8) | 4.7 | — |
| embodiment 11 | 102.9 (78.7) | 4.7 | — |
| embodiment 12 | 97.3 (95.4) | 4.5 | — |
| embodiment 13 | 109.4 (99.4) | 4.4 | — |
| embodiment 14 | 110.4 (98.6) | 4.5 | — |
| embodiment 15 | 95.4 (80.0) | 4.5 | — |
| embodiment 16 | 102.0 (72.2) | 3.1 | — |
| embodiment 17 | 128.6 (110.7) | 3.2 | — |
| embodiment 18 | 100.6 (103.5) | 3.2 | — |
| embodiment 19 | 104.6 (95.8) | 4.0 | — |
| embodiment 20 | 97.5 (87.9) | 4.2 | — |
| embodiment 21 | 95.3 (84.5) | 4.4 | — |
| embodiment 22 | 91.3 (73.2) | 4.4 | — |
| embodiment 23 | 106.8 (85.2) | — | 50.8 |
| embodiment 24 | 101.4 (76.5) | — | 48.0 |
| embodiment 25 | 104.7 (74.2) | — | 45.9 |
| embodiment 26 | 97.1 (75.1) | — | 39.9 |
| embodiment 27 | 100.9 (89.6) | — | 42.9 |
| embodiment 28 | 96.5 (75.7) | — | 37.3 |
| comparative example 1 | particle size measurement was impossible | — | — |

Diameter: averaged size of three measurement values, i.e., size by a light scattering, size by a weight and size by the number, when measuring a size.
Wt.: size by a weight
encapsulation ratio (%): the encapsulation ratios of the iron oxide and drug indicate the average value that were measured three times. Error range: ±0.2

Figure 8:
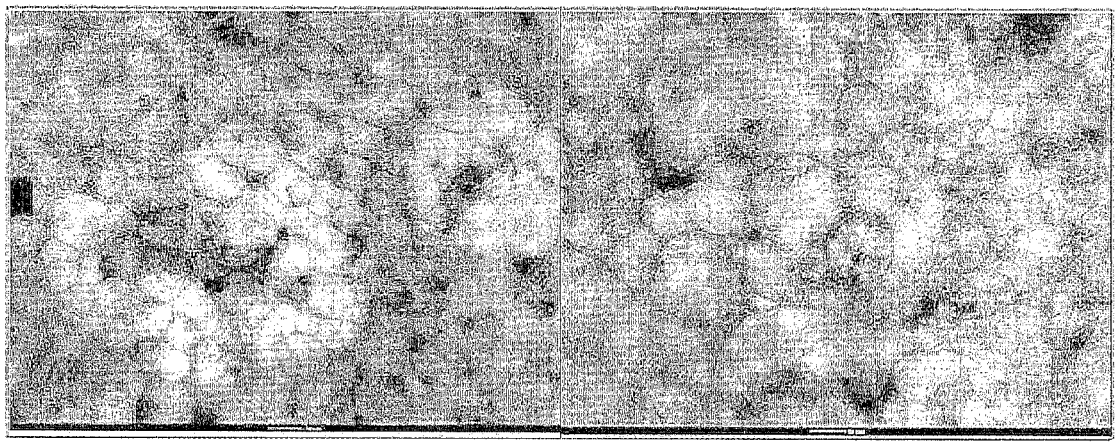
FIGS. 8 to 10 are photographs showing structures of polymer micelle type contrast medium and anti-cancer medicine prepared according to an embodiment of the invention, the structures being measured using a cryo-TEM (BIO-TEM (Biological Transmission Electron Microscopy) available from FEI CO. (USA); Model No. Tecnai G2 Spirit))
Figure 9:
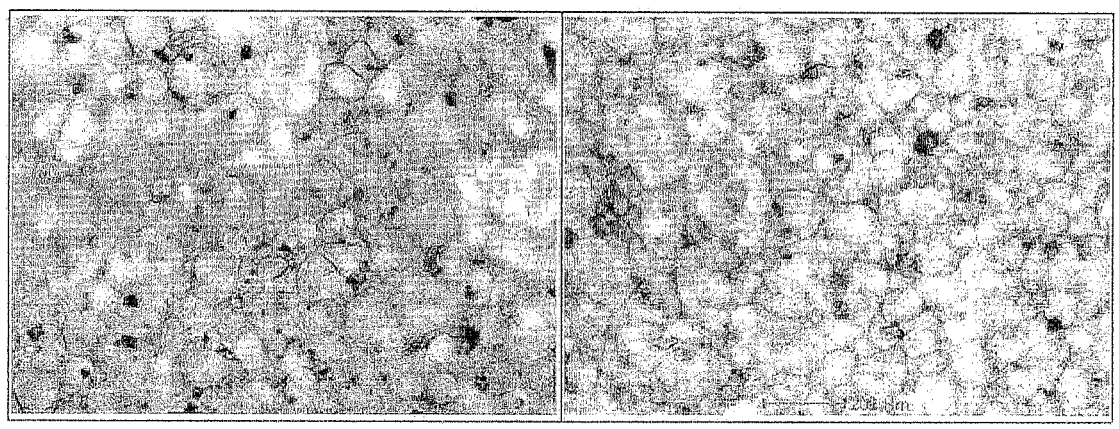
Figure 10:
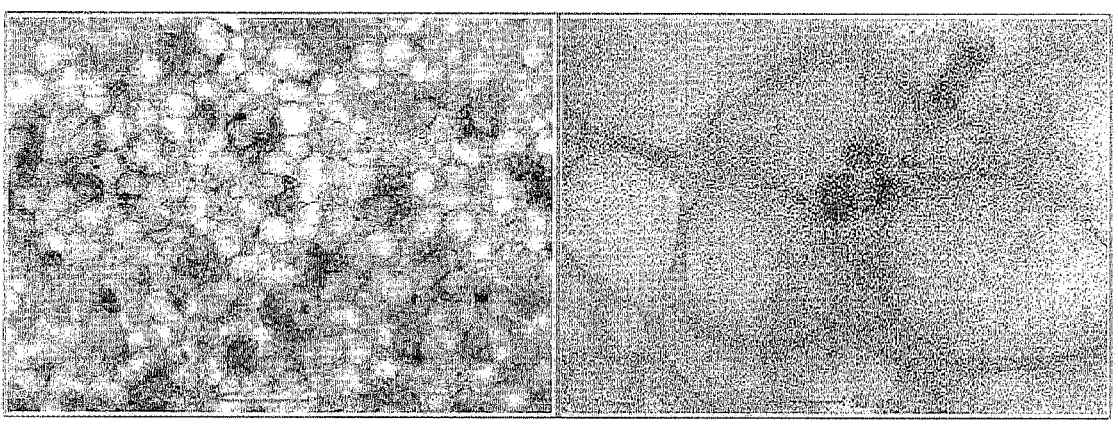

The cryo-TEM of the polymer micelle type contrast medium and anti-cancer medicine and PEO-TMA-FA polymer, which were prepared according to the embodiments 4 and 23, was measured using a BIO-TEM (Biological Transmission Electron Microscopy, Model No. Tecnai G2 Spirit, FEI CO. (USA)) in accordance with a following process. First, the gelatin was mixed in a physiological salt solution to be 10%, so that the gelatin was made to be liquid phase at 37° C. The liquid phase gelatin and the polymer micelle sample were mixed well, which were then solidified at room temperature. Then, the sample was made to be a piece having a thickness of 70 nm using an ultra microtom. Then, it was put on a carbon coated grid and a TEM measurement was then performed. A result of the measurement is shown in FIGS. 8 to 10. FIG. 8 shows the measurement of a structure of polymer PEO-TMA-FA, and FIGS. 9 and 10 show the measurements of structures of polymer micelles prepared according to the embodiments 4 and 23, respectively. As shown in Figs., it could be seen that the contrast medium and the anti-cancer medicine prepared according to the embodiments had a micelle type and were nano-particles having a size of 50~100 nm.

EXPERIMENTAL EXAMPLE 2

Measurement of Contrast Effect of the Polymer Micelle Type Contrast Medium

Figure 11:
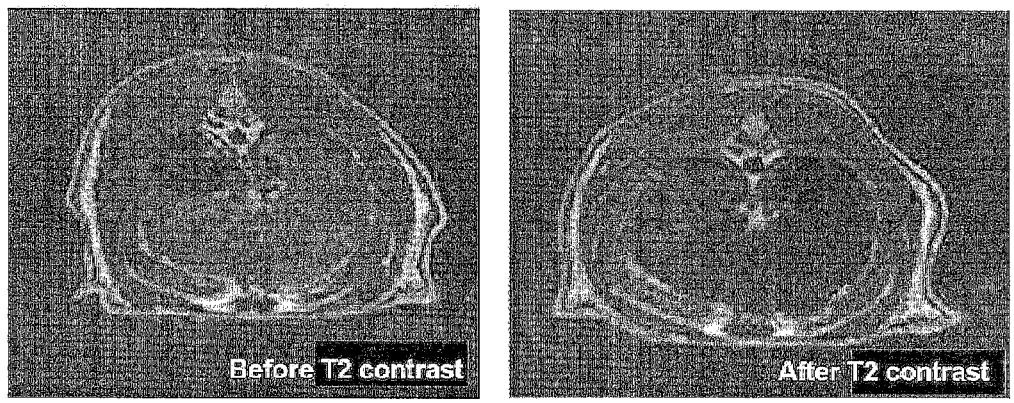
FIGS. 11 to 14 are photographs showing a contrast effect of a polymer micelle type contrast medium according to an embodiment of the invention.
Figure 12:
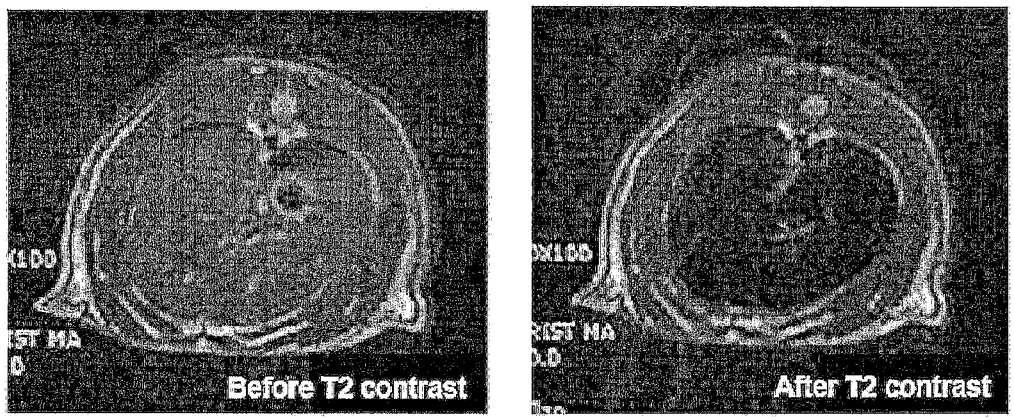
Figure 13:
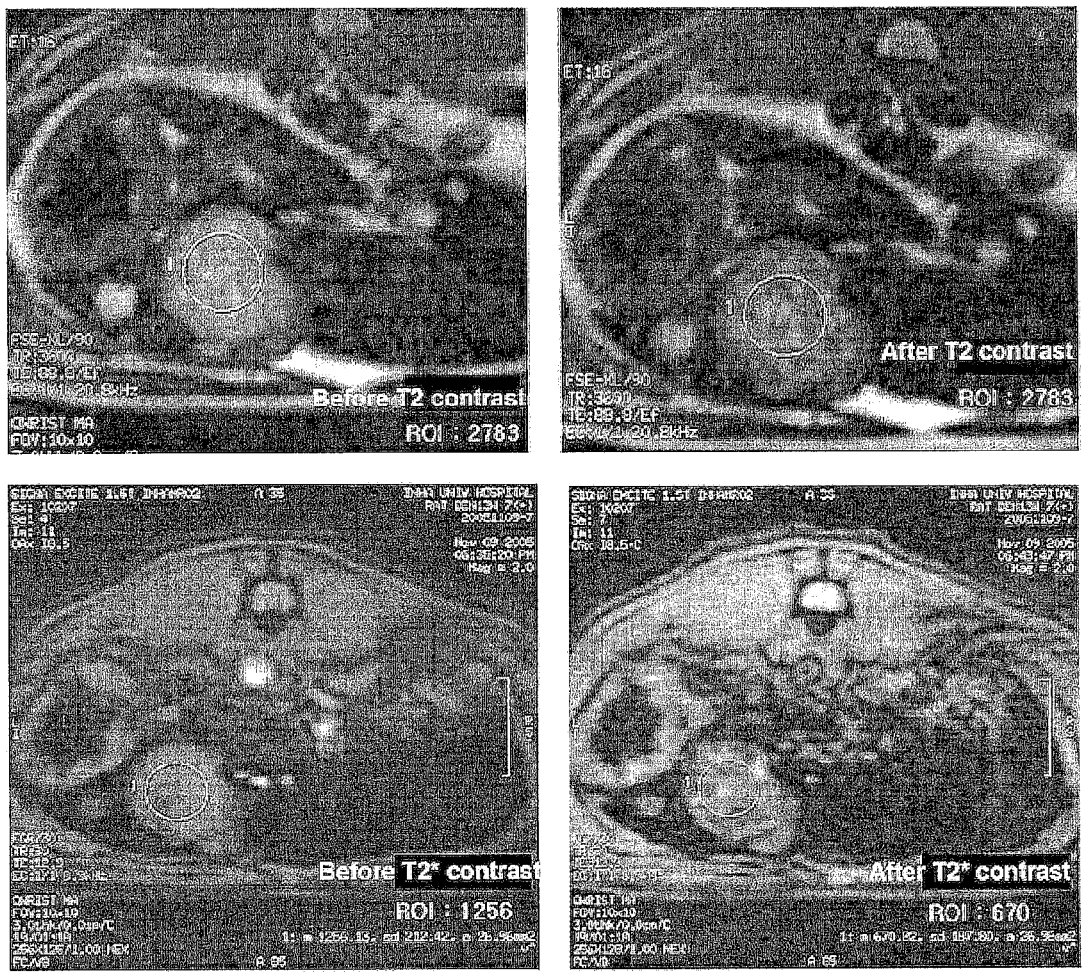
Figure 14:
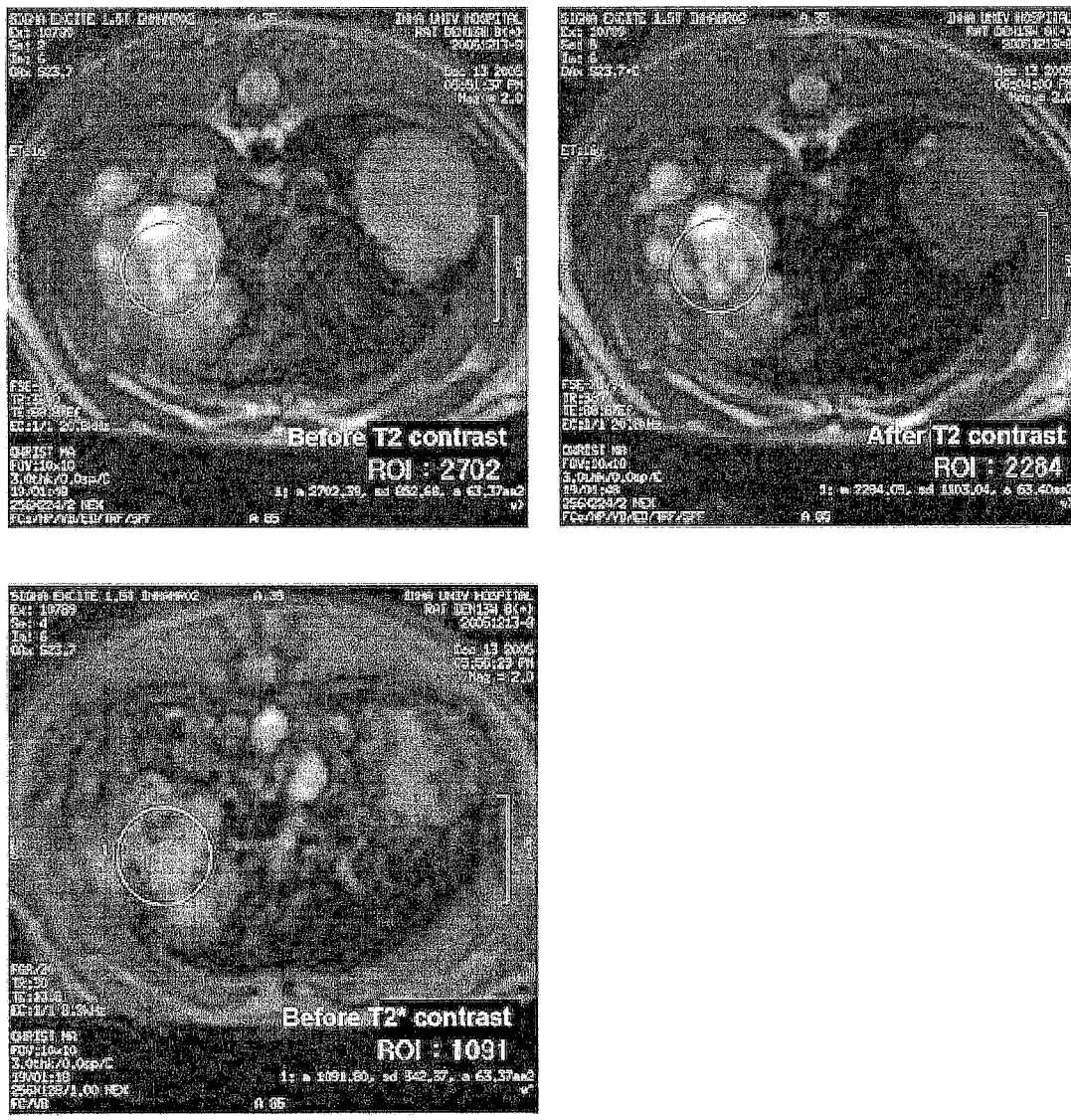

Liver Contrast Effect of a Normal Mouse
In order to examine a contrast effect in a liver of a mouse, a male SD-rat was anesthetized. Then, the contrast media prepared according to the embodiments 10 and 21 were respectively injected by 0.9 cc (fixed quantity) to the tail vein, so that MR images were obtained. Among them, the results of the embodiments 10 and 21 are shown in FIGS. 11 and 12. The left photograph is an image before T2 contrast and the right photograph is an image after T2 contrast. It can be seen in the T2 weighted image that the signal intensity of the liver was reduced after injecting the MR contrast medium. In other words, it can be seen that the contrast media are suitable for the MR contrast medium for liver.
Hepatoma Contrast of Hepatoma Model Mouse
In order to make a hepatoma model, the water in which diethyl nitrosamine was diluted in a ratio of 1:10,000 was supplied to 8 weeks old SD-rat every day for 12 weeks until the tumor occurred. After checking that the hepatoma occurred in the rat after 10 weeks breeding, the MR contrast media prepared according to the embodiments 10 and 21 were respectively injected by 2 mL/kg (fixed quantity) to the tail vein of the rat. As a result, the contrast effect on the hepatoma in the rat could be seen in the T2-weighted image and T2*-weighted image. Among them, the results of the embodiments 10 and 21 are shown in FIGS. 13 and 14. As shown in FIGS. 13 and 14, while a signal intensity in which liver parenchyma is low is shown, a signal intensity in which the hepatoma is relatively high is shown, so that the hepatoma can be easily found and the same effect as Resovist that is used in the market is obtained. In addition, since the contrast medium is nano-particles containing the iron, the nano-particles are selectively ingested into the hepatoma. Therefore, it can be expected that a region of interest (ROI) of the signal intensity of the hepatoma will be reduced. Actually, as shown in FIGS. 13 and 14, the ROI of the signal intensity was reduced in the hepatoma.

EXPERIMENTAL EXAMPLE 3

MIT Measurement of the Polymer Micelle Type Anti-Cancer Medicine: Toxicity Test

Figure 15:
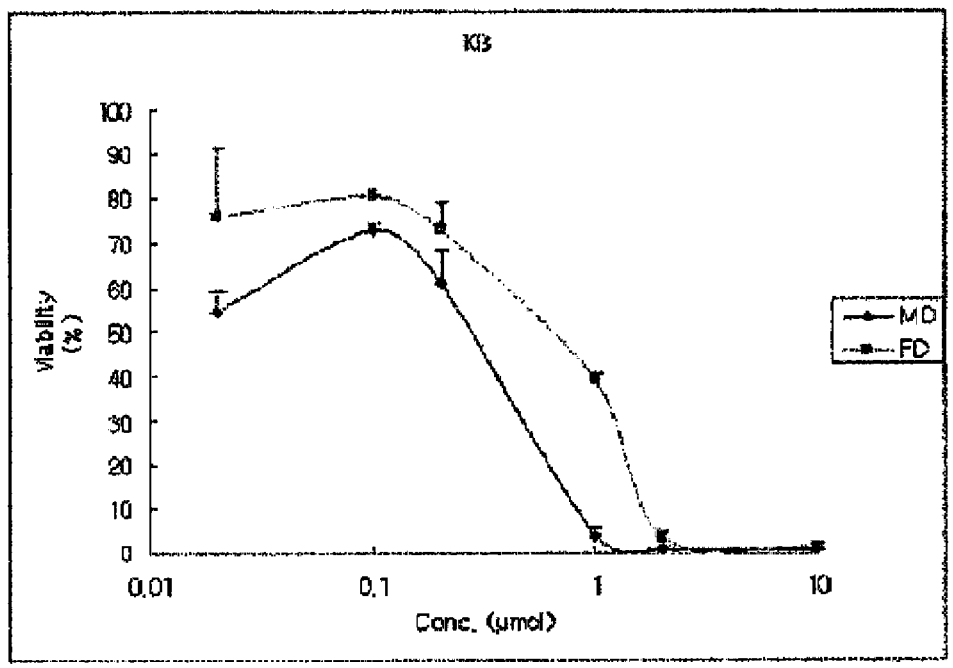
FIG. 15 is a graph showing a cytotoxicity test of a polymer micelle type anti-cancer medicine according to an embodiment of the invention.
Figure 16:
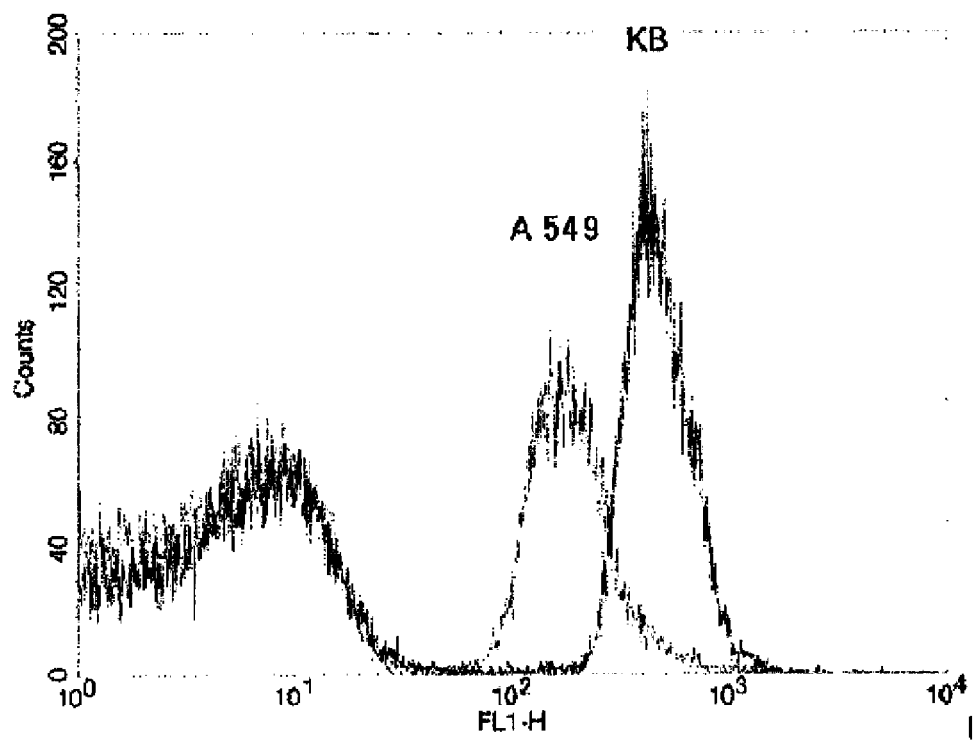
FIG. 16 is a graph showing an endocytosis test of a polymer micelle type anti-cancer medicine according to an embodiment of the invention.

Toxicity Test
The toxicity of the biodegradable polymer micelle type anti-cancer medicine was measured in KB (human epidermal carcinoma) cells and A549 (human lung carcinoma) cells. The cells were diluted with 200 μL RPMI1640 $5 \times 10^4$ cells/mL, and were seeded in 96-well cell culture plates. After 24 hours, the doxorubicin free solution (FD), the blank micelles and the anti-cancer medicine having the doxorubicin encapsulated therein (micelle doxorubicin, MD), which was prepared in the embodiment 23, were treated to the cell culture medium in various concentrations and then incubated for 48 hours (37° C., 5% $CO_2$). After the incubation, the culture medium 100 μL in which 20 μL MTT (tetrazolium salts) solution was contained was applied to each well after washing it with PBS three times, and then was again incubated for 4 hours. 100 μL DMSO was applied to each well and the plates were strongly stirred so as to dissolve the cells. The absorbency was measured at 540 nm using the ELISA reader so as to check a degree of the cytotoxicity. The MTT measurement result is shown in FIG. 15. In FIG. 15, the MD shows the micelle solution that is prepared according to the embodiment 23. As a check result of the cytotoxicity, it could be seen that the MD had a higher ability of killing the cancer cells in the range of tested concentrations, as compared to the FD (free doxorubicin).
Mechanism Study
The KB (human epidermal carcinoma) cells and A549 (human lung carcinoma) cells were obtained from a Korean Cell Line Bank. Each cell line was cultured in RPMI 1640 culture medium (10% fetal bovine serum, 100 units/mL penicillin, streptomycin of 0.1 mg/mL). In culturing the cells, the conditions of 37° C., 5% $CO_2$ and 90% humidity were maintained all the time. In the folate competitive inhibition test, the folate was added.
The endocytosis amounts of the doxorubicin free solution (FD) and PEO-TMA-FA/Fe/Dox (embodiment 23) were compared in the KB cells (or Caco-2, HepG2) in which the folate receptors were much expressed and the A549 in which the folate receptors were not expressed. The free doxorubicin (20 μM) and the PEO-TMA-FA/Fe/Dox (20 μM) prepared according to the embodiment 23 were incubated for 3 hours together with the folic acid (2 mM), which were then washed with PBS three times. Then, the cells were collected. After that, it was measured the doxorubicin amounts, which were introduced in the cells, with the quantitative method described above. The result is shown in FIG. 16. As can be seen from the result, the doxorubicin was ingested in the KB cells much more than in the A549. In other words, the targeting function of the folate could be indirectly checked.

EXPERIMENTAL EXAMPLE 4

Figure 17:
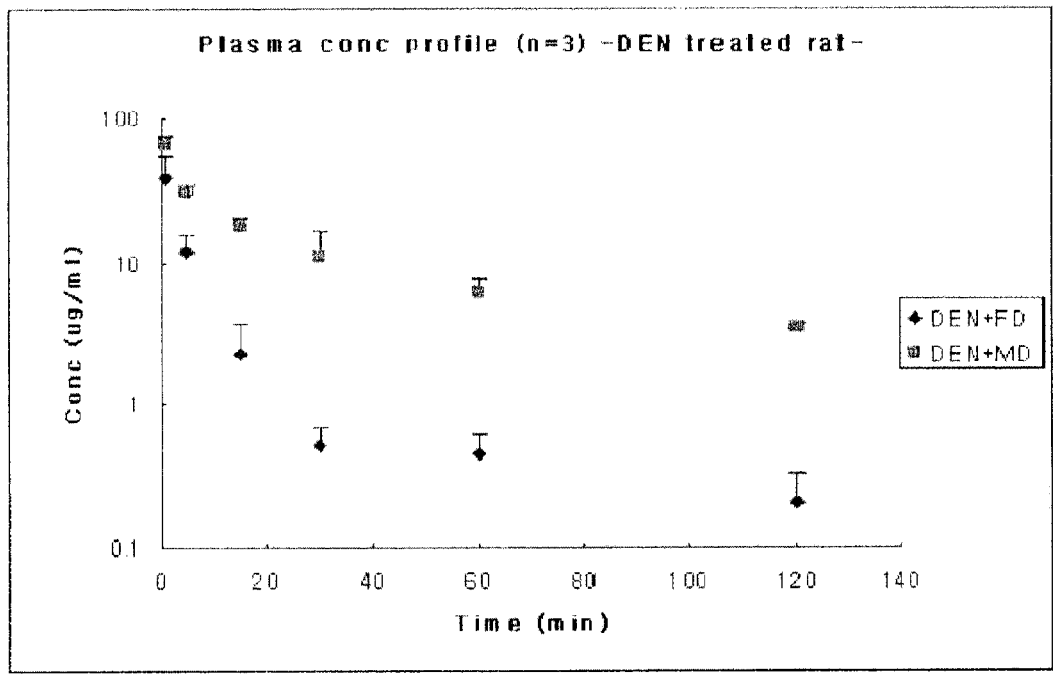
FIGS. 17 and 18 are graphs showing a change in a plasma concentration as time goes by, after a polymer micelle type anti-cancer medicine is administrated.
Figure 18:
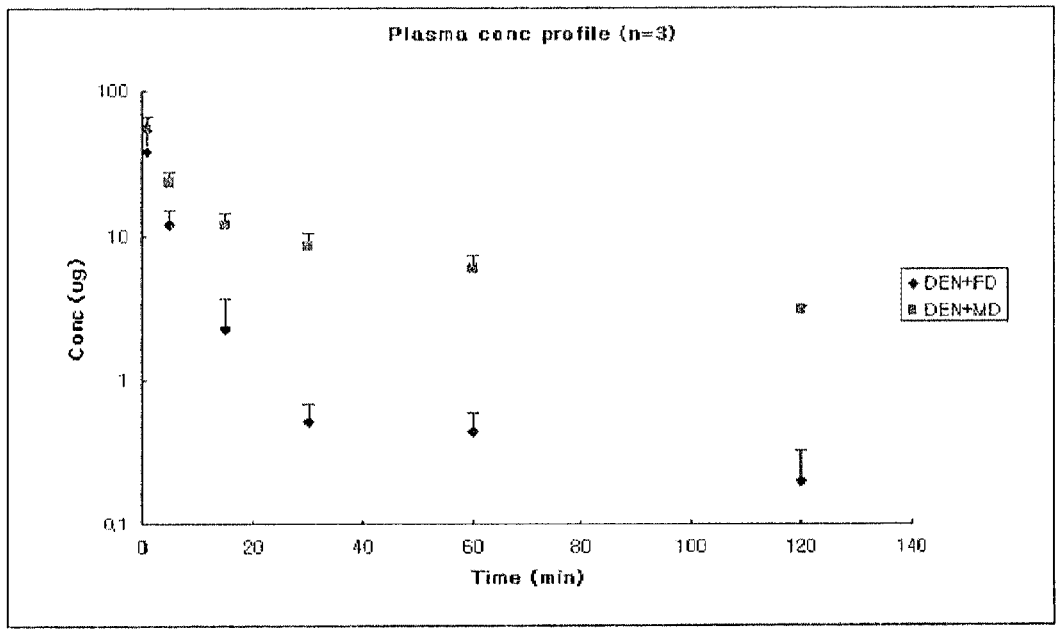

Sustained-Release Check of the Polymer Micelle Type Anti-Cancer Medicine/Pharmacokinetics Study Change in Blood Plasma Concentration as Time Goes by
The Sprague Dawley (SD) adult male rat was slightly anesthetized with ketamine and acepromazine. Then, the femoral vein was subject to cannulation with physiological salt solution and the artery was subject to cannulation with polyethylene tubing (PE-50, intramedic, Clay-Adams) in which the physiological salt solution of 40 I.U./mL was filled, for which the heparin treatment was performed. After the proper recovery time has elapsed, the doxorubicin free solution and the doxorubicin of the polymer micelle formulation prepared according to the embodiment 23 were administered into the vein by 10 mg/kg (on the basis of the doxorubicin), respectively. At 0 (blank), 1, 5, 15, 30, 60 and 120 minutes after the administration, the blood 0.3 mL was respectively sampled, which was then centrifugally separated (13,000 rpm, 3 minutes) to separate about 0.1 mL of the blood plasma. Then, it was deproteinated and then analyzed with HPLC.
It was used the HPLC method using a reverse phase C-18 column (Shim-pack CLS-ODS, 4.6 mm I.D. 250 mm L., 5 m particle diameter). To the sampled blood plasma 0.1 mL were applied an internal standard material solution 50 μL (2 μL/mL daunomycin), the methanol 100 μL and the ethyl acetate 1.0 mL. The mixture solution was subject to vortexing for 3 minutes and centrifugally separated for 3 minutes (3,000 rpm) to take the organic layer only (1.0 mL), which was then dried with speed-vac. The remnants were re-composed into a moveable phase of 300 μL and 100 μL of which was then directly injected to a HPLC system. As the moveable phase of the HPLC system, a solution of the deionized water (pH=2.5 by phosphoric acid):acetonitrile=6:4 was used and a flow rate was 1 mL/min. As a HPLC detection method, a fluorescent analysis method was used at 470 nm excitation wavelength and 565 nm emission wavelength. The doxorubicin standard solution for making a calibration curve was made by dissolving it in the methanol so that it became 0.05, 0.1, 0.5, 1 and 3 μg/mL. When preparing a biological sample calibration curve, the standard solution 100 μL of doxorubicin 0.05, 0.1, 0.5, 1 and 3 μg/mL was put instead of methanol 100 μL for pre-treatment. Then, a calibration curve was made from which the doxorubicin in the blood plasma was obtained. The result is shown in FIGS. 17 and 18. FIG. 17 shows a result of the embodiment 23 and FIG. 18 shows a result of the embodiment 26. As shown in FIGS. 17 and 18, when the polymer micelle type anti-cancer medicine prepared according to the embodiments 23 and 26 was administrated, the doxorubicin concentration in the blood was increased every sampling time, as compared to a case where the FD (free doxorubicin) was administrated. According to an area under the curve (AUC) obtained from the blood-level vs. time plot, the AUC was increased by five times or more for the polymer micelle type anti-cancer medicine. Thereby, a total clearance (CL), which is obtained by dividing the dose by AUC, was also decreased (refer to a table 2). This means that the polymer micelle type anti-cancer medicine was exposed in the body longer than the FD (free doxorubicin).

TABLE 2

| PK parameters | FD | MD (embodiment 23) | MD (embodiment 26) |
|---|---|---|---|
| $t_{1/2}$ (min) | 51.58 ± 34 | 72.18 ± 38.8 | 69.95 ± 30.4 |
| AUC (min * μg/mL) | 291 ± 98 | 1652 ± 63 | 1467 ± 25 |
| CL (mL/min/kg) | 37.89 ± 15.8 | 6.06 ± 0.24 | 6.00 ± 0.54 |
| Vss (mL/kg) | 965.9 ± 593.86 | 484.9 ± 230.84 | 512.4 ± 241.54 |

$t_{1/2}$: half-life
AUC: area under the curve in the plasma concentration time plot
CL: total clearance, lost clearance of drug
Vss: weight volume, volume of distribution at steady state

EXPERIMENTAL EXAMPLE 5

Biodistribution Test

Figure 19:
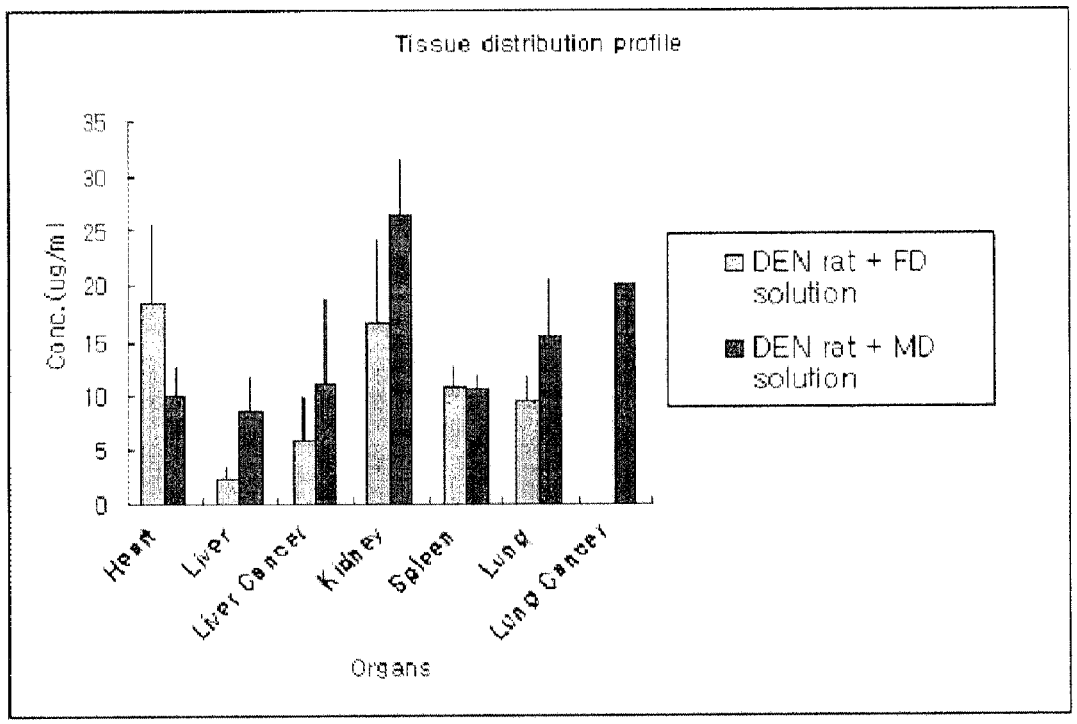
FIGS. 19 and 20 show a result of a bio-distribution test measuring a degree that the drug is distributed in each organ, after a polymer micelle type anti-cancer medicine is administrated.
Figure 20:
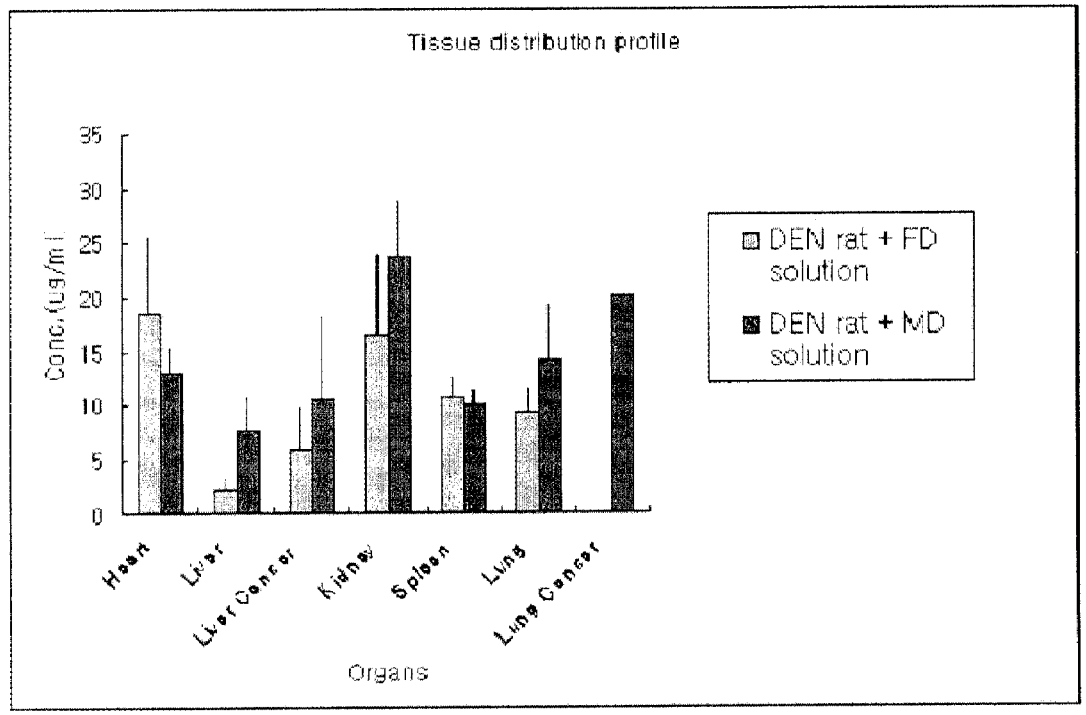

The SD adult male rat was slightly anesthetized with ether. Then, the femoral vein was subject to cannulation with polyethylene tubing (PE-50, intramedic, Clay-Adams). After stabilizing for about 30~60 minutes, the polymer micelle type anti-cancer medicines (MD) prepared according to the embodiments 23 and 26 and the free doxorubicin (FD) were administrated in the vein by 10 mg/kg (on the basis of the doxorubicin), respectively. At 2 hours after the administration, the rat was subject to decaptitation and the liver, heart, kidney, lung and spleen were removed which tissues were then taken in an amount of about 1 g. The tissues were washed with cold saline (0.9% NaCl). After measuring the weights of the respective tissues, the cold saline (0.9% NaCl) corresponding to the four times weight was applied and the tissues were homogenized for 3 minutes with a tissue homogenizer (Ultra-Turrax T25, Janke & Kunkel, IKA-Labortechnik) and centrifugally separated (3,000 rpm, 10 minutes) to take supernatant fluid 0.1 mL. For the fluid, the doxorubicin biodistribution concentrations in the respective tissues were measured with the HPLC. The results are shown in FIGS. 19 and 20. FIG. 19 shows a result of the embodiment 23 and FIG. 20 shows a result of the embodiment 26.

As shown in FIGS. 19 and 20, for the polymer micelle type anti-cancer medicine according to the invention, the tissue biodistribution in most of the tissues was higher than the FD. However, for the heart exhibiting the side effects of the doxorubicin, the tissue biodistribution was smaller than the FD, so that the side effects are expected to be smaller. In addition, for the liver or lung, the MD was much distributed in the cancer tissue than in the normal tissue.

EXPERIMENTAL EXAMPLE 6

Measurement of Doxorubicin Content in the Polymer Micelle Type Anti-Cancer Medicine According to the Invention Doxorubicin hydrochloride (Boryung Inc.) 10 mg was precisely taken in a 100 mL flask into which DMSO 80 mL was then put and dissolved by stirring for 10 minutes. Then, dimethylsulfoxide was put so that the solution became 100 mL. The solution 10 mL was taken to which the moveable phase was then put so that the solution was 100 mL. This solution was used as a standard solution. The polymer micelle 10 mg, which was prepared in the embodiment 23, was precisely taken in a 100 mL flask into which DMSO 10 mL was then put and dissolved by stirring for 10 minutes. Then, to the solution was put the moveable phase so that the solution became 100 mL. This solution was used as a sample solution. In the analysis, the sample solution and the standard solution were tested in a following test condition according to the liquid chromatography method, so that the peak areas At and As of the doxorubicin were obtained (the pre-treatment and analysis process were rapidly performed in a position where the light was generally shielded).

Amount (mg) of Doxorubicin ($C_{27}H_{29}NO_{11}$)=amount (mg) of doxorubicin hydrochloride standard=0, 9371×$A_t/A_s$)×1/10

0.9371: molecular weight of doxorubicin (543.53)/molecular weight of doxorubicin hydrochloride (579.99)

Figure 21:
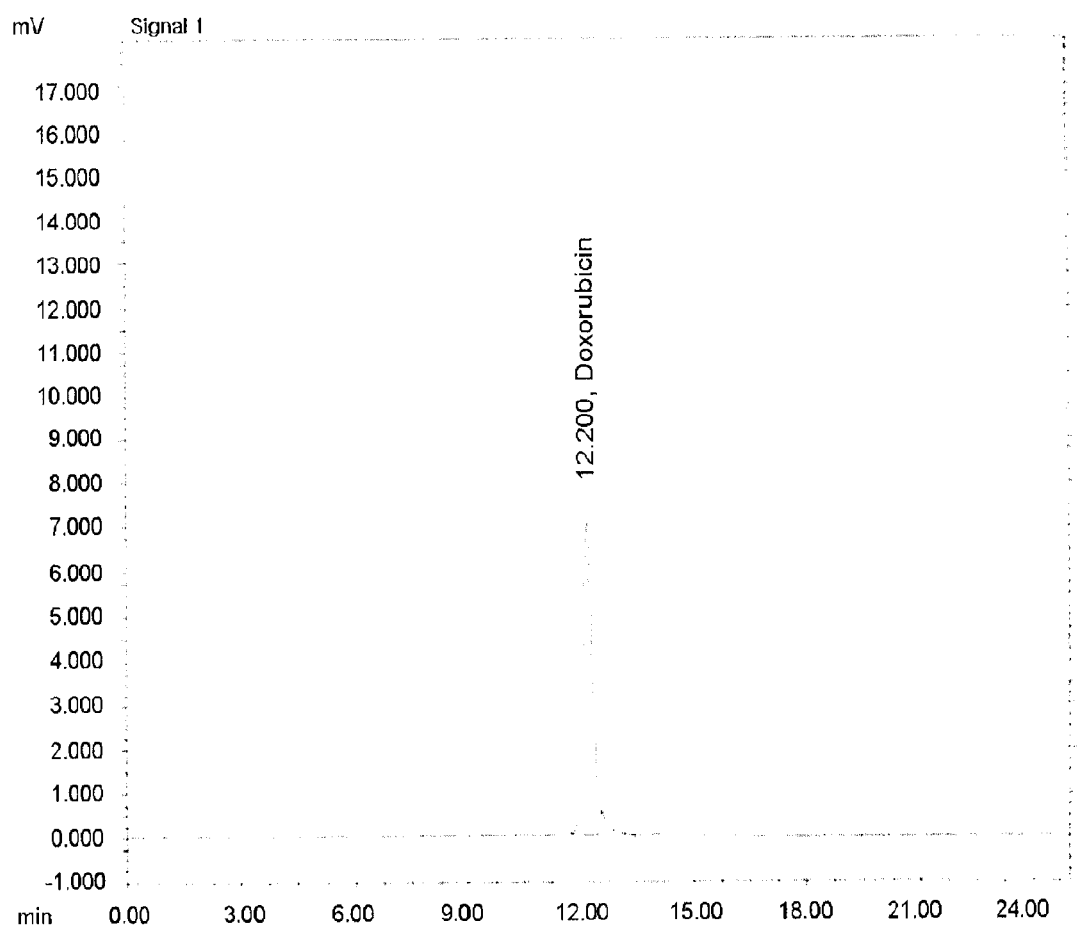
FIG. 21 shows a characteristic peak of doxorubicin.
Figure 22:
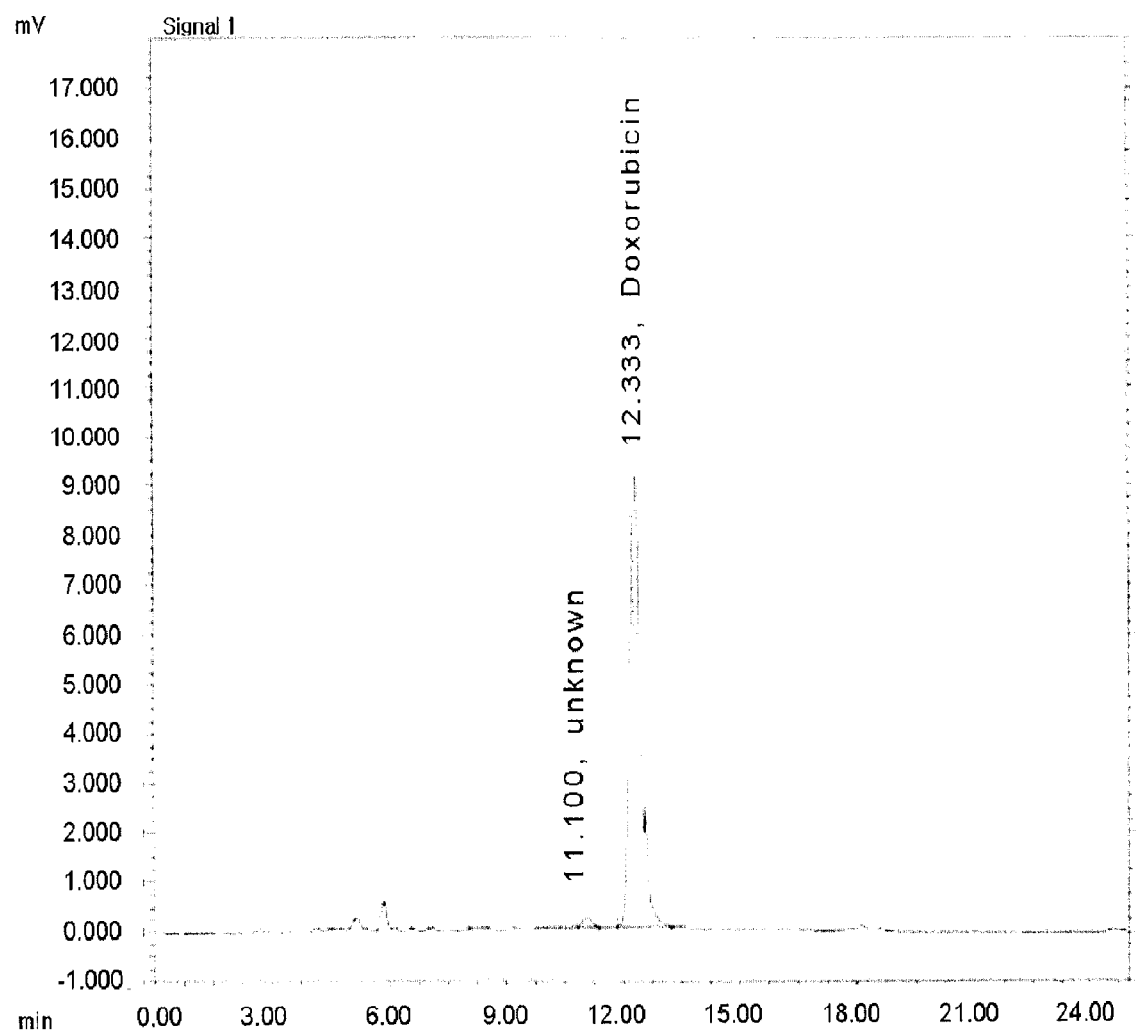
FIG. 22 shows a HPLC peak of a polymer micelle type anti-cancer medicine according to an embodiment of the invention.

A SHIM-PACK VP-ODS 250×4.6 column was used. As the moveable phase, the solution of $H_2O$:ACN=7:3 was used, which was quantified with HPLC. At this time, the flow rate was 1.0 mL/min., the temperature was a room temperature and a fluorescent detector (Ex.:480 Em.:560 nm) was used as the detector. FIG. 21 shows a characteristic peak of the doxorubicin and FIG. 22 shows a HPLC peak of the polymer micelle type anti-cancer medicine.

EXPERIMENTAL EXAMPLE 7

Comparison of Encapsulation Ratios Depending on the Method of Preparing the Doxorubicin Base Preparation Method Using DMSO Only The doxorubicin hydrochloride 10, 20, 40 and 60 mg were put into the 20 mL vials to which DMSO 1 mL was then added to dissolve it. To this solution was put the triethylamine (2 eq.), which was then stirred for about 10 minutes. The polymer (PEO-TMA-FA) 750 mg prepared in the preparation example 1, the iron oxide 250 mg and water 10 mL were added to a 100 mL beaker to which the doxorubicin was then put. The beaker was covered with foil and was subject to sonication for 2 hours. Then, the solution was put in a 50 mL conical tube and was subject to a centrifugal separation at 2,000 rpm for 10 minutes to prepare a sample. For dialysis, mannitol 1,000 g was dissolved in 20 l DDW to prepare a 5% mannitol solution. At this time, pH thereof was adjusted to be 7.4 with NaOH. Then, the sample for which the centrifugal separation was completely performed was put in a dialysis membrane (MWCO=3,500), which was previously steeped in water. Then, the membrane was bound at its front and rear with a holder, which was then immersed in a dialysis receptacle having solution therein. Then, it was stirred at 500 rpm for 24 hours and was subject to the dialysis while replacing the 5% mannitol solution. The sample for which the dialysis was completely performed was put and frozen in a deep freezer. After that, the sample was lyophilized for 3 days with a freeze-dryer, thereby preparing the micelle having the doxorubicin encapsulated therein.

Use of Co-Solvent (DMSO+Water)

Figure 23:
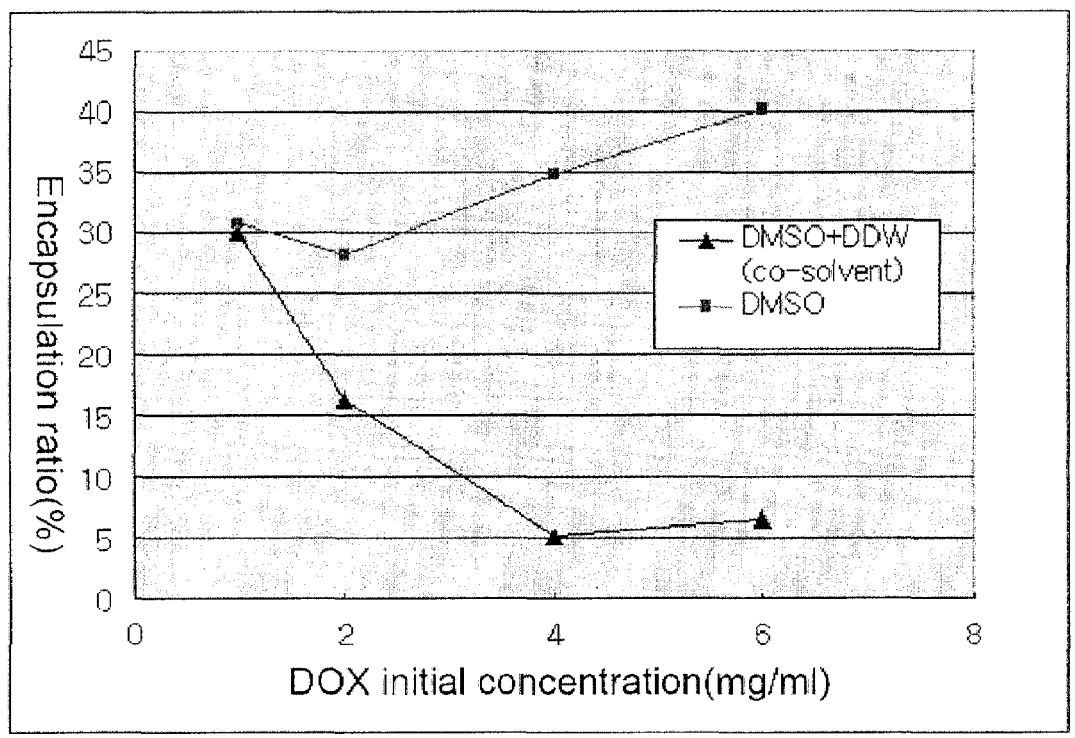
FIG. 23 is a graph showing a difference of encapsulation ratios between a case where only DMSO is used as a solvent and a case where a mixed solution of DMSO and water is used as a solvent.

The doxorubicin hydrochloride 10, 20, 40 and 60 mg were put into the 20 mL vials to which DMSO 0.5 mL was then added to dissolve it. To this solution was put the water 3 mL and the triethylamine (2 eq.), which was then stirred for about 10 minutes. The polymer (PEO-TMA-FA) 750 mg prepared in the preparation example 1, the iron oxide 250 mg and water 7 mL were added to a 100 mL beaker to which the doxorubicin was then put. The beaker was covered with foil and was subject to sonication for 2 hours. Then, the solution was put in a 50 mL conical tube and was subject to a centrifugal separation at 2,000 rpm for 10 minutes to prepare a sample. For dialysis, mannitol 1,000 g was dissolved in 20 1DDW to prepare a 5% mannitol solution. At this time pH thereof was adjusted to be 7.4 with NaOH. Then, the sample for which the centrifugal separation was completely performed was put in a dialysis membrane (MWCO=3,500), which was previously steeped in water. Then, the membrane was bound at its front and rear with a holder, which was then immersed in a dialysis receptacle having solution therein. Then, it was stirred at 500 rpm for 24 hours and was subject to the dialysis while replacing the 5% mannitol solution. The sample for which the dialysis was completely performed was put and frozen in a deep freezer. After that, the sample was lyophilized for 3 days with a freeze-dryer, thereby preparing the micelle having the doxorubicin encapsulated therein. The encapsulation ratios of the polymer micelle type anti-cancer medicine are shown in tables 3 and 4 and FIG. 23. The table 3 shows a result of the case where DMSO only was used, and the table 4 shows a result of the case where both DMSO and water were used. As shown in the table 3 and FIG. 23, the encapsulation ratio was higher in the case where the DMSO only was used.

TABLE 3

| weight of doxorubicin (mg) | particle size (nm) | encapsulation ratio (%) | encapsulation amount (mg/mL) |
| --- | --- | --- | --- |
| 10 | 62.9 | 30.77 | 0.3 |
| 20 | 63 | 28.18 | 0.56 |
| 40 | 61.1 | 34.81 | 1.39 |
| 60 | 71.9 | 40.2 | 2.4 |

TABLE 4

| weight of doxorubicin (mg) | particle size (nm) | encapsulation ratio (%) | encapsulation amount (mg/mL) |
| --- | --- | --- | --- |
| 10 | 62.4 | 29.98 | 0.3 |
| 20 | 69.2 | 16.41 | 0.33 |
| 40 | 64.7 | 5.23 | 0.21 |
| 60 | 49.2 | 6.67 | 0.4 |

EXPERIMENTAL EXAMPLE 8

Figure 24:
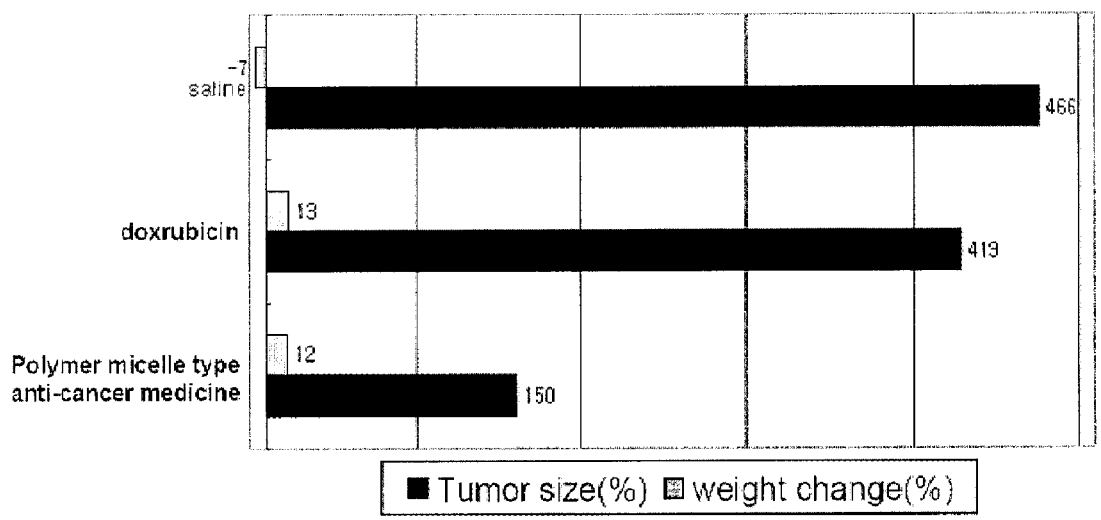
FIGS. 24 and 25 are graphs showing measurement results of tumor growth after a polymer micelle type anti-cancer is administrated in a rat.
Figure 25:
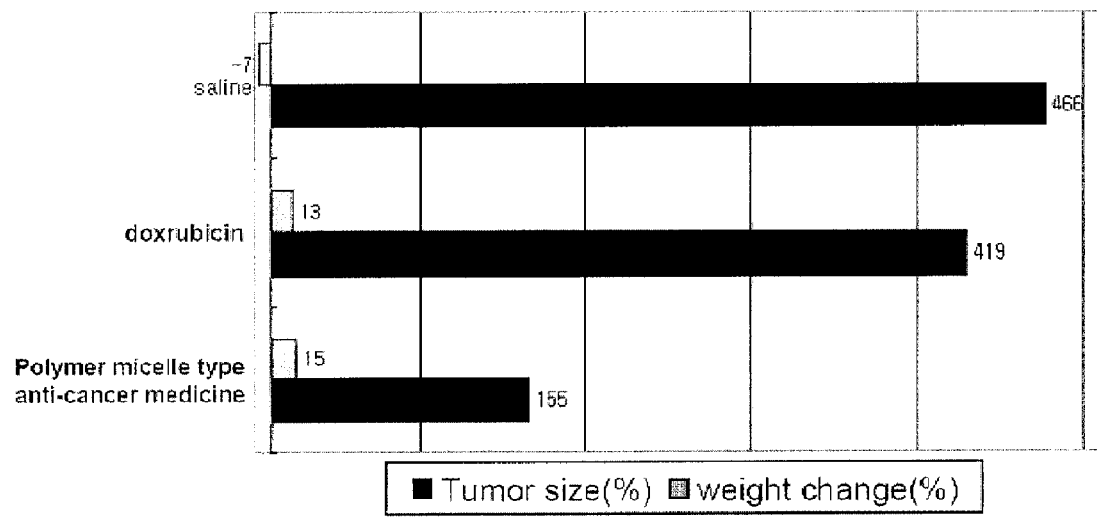
Figure 26:
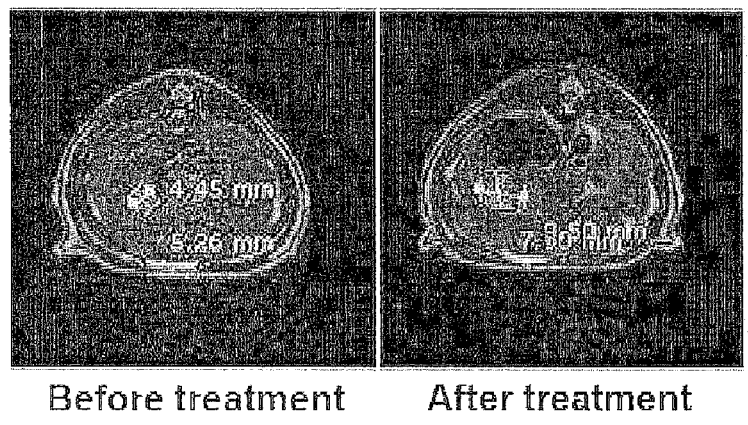
FIGS. 26 and 27 are photographs showing tumor growth after a polymer micelle type anti-cancer is administrated in a rat.
Figure 26:
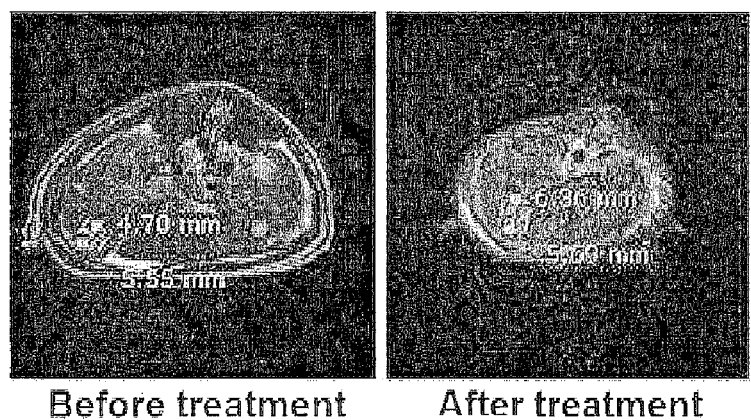
Figure 26:
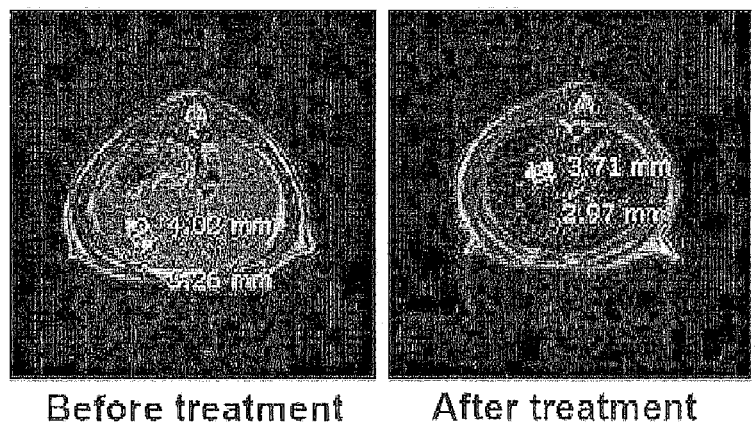
Figure 27:
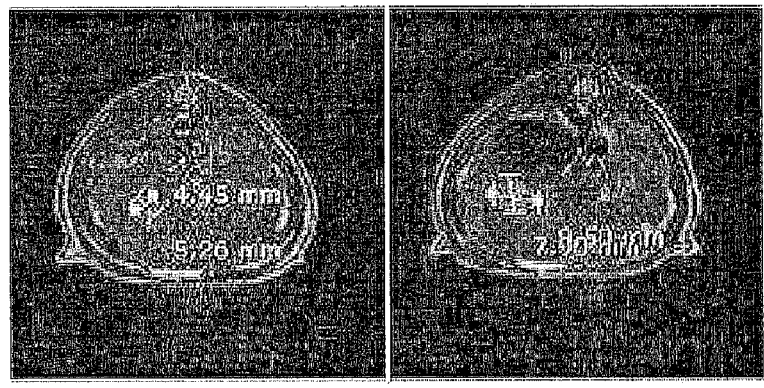
Figure 27:
Figure 27:
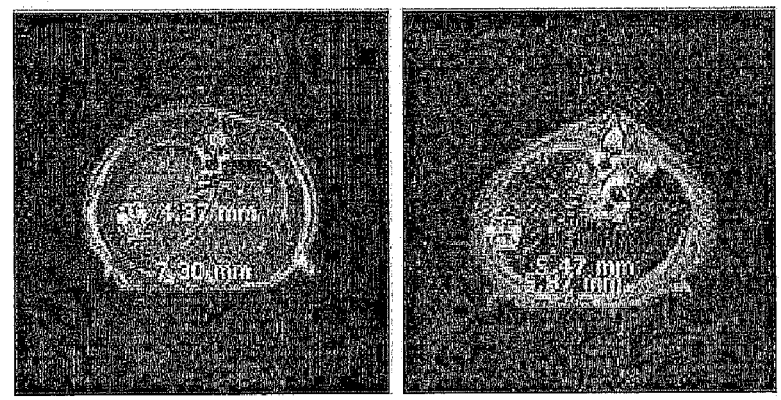

Measurement of Tumor Growth after the Polymer Micelle Type Anti-Cancer Medicine is Administrated in the Rat In order to make a hepatoma model, the water in which diethyl nitrosamine was diluted in a ratio of 1:10,000 was supplied to 8 weeks old SD-rat every day for 12 weeks until the tumor was generated. The hepatoma was formed by 100%. It was checked with MRI whether the tumor was after 10 weeks breeding. When the size of the largest tumor was a diameter of 5 mm, the physiological salt solution, the doxorubicin (ADM), the polymer micelle type anti-cancer medicines (YCC) prepared according to the embodiments 23 and 26 were respectively injected by 2 mg/kg to the tail vein of the rat. Again, the MRI photographing was made. The phleboclysis was performed three times every 5 days. Then, at one week after the last phleboclysis, the sizes of the tumors were compared through the MRI photographing. FIG. 24 shows changes in the size of the tumor and the weight if the embodiment 23, and FIG. 25 shows changes in the size of the tumor and the weight of the embodiment 26. FIG. 26 is a MRI photograph of the embodiment 23 and FIG. 27 is a MRI photograph of the embodiment 26. As shown in FIGS. 24 and 25, it could be seen that the polymer micelle type anti-cancer medicine according to the invention most inhibited the tumor growth. In addition, the polymer micelle type anti-cancer medicine according to the invention did not cause the loss of weight. As shown in FIGS. 26 and 27, the size of the tumor became larger for the physiological salt solution and the doxorubicin. However, when the polymer micelle formulation according to the invention was administrated, the size of the tumor was much reduced.

EXPERIMENTAL EXAMPLE9

Measurement of Change in the Weight of the Rat Resulting from the Administration of the Polymer Micelle Type Anti-Cancer Medicine after Transplanting the Tumor After the polymer micelle type anti-cancer medicines prepared according to the embodiments 23 and 26 are injected to the tail vein of the rat by 2 mg/mL, it was measured a change in the weight of the rat in accordance with the drug administration. The results are shown in FIGS. 24 and 25. FIG. 24 shows a result of the embodiment 23 and FIG. 25 shows a result of the embodiment 26. As shown in FIGS. 24 and 25, there was no dead rat after the drug administration. In other words, the survival rate was 100%.

INDUSTRIAL APPLICABILITY

The polymer micelle type anti-cancer medicine according to the invention can treat the cancer and serve as a contrast medium, thereby diagnosing the cancer and monitoring the progress of the disease.

While the invention has been shown and described with reference to certain preferred embodiments thereof, it will be understood by those skilled in the art that various changes in form and details may be made thereto without departing from the spirit and scope of the invention as defined by the appended claims.

The invention claimed is:

1. A polymeric anti-cancer medicine having a micelle structure performing diagnosis and treatment of cancer at the same time and comprising, a chain end functionalized polymer expressed as a following chemical formula 1:

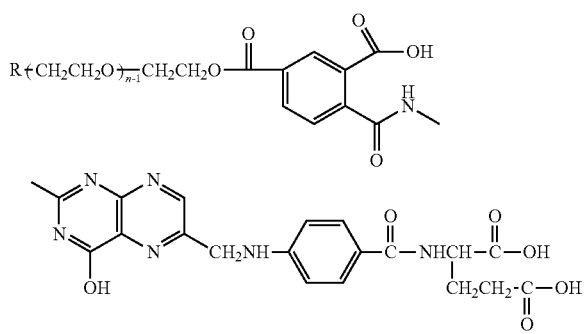

wherein, R is, n-butyl and n is an integer of 10 to 500;
a contrast material; and
a chemotherapeutic agent,
wherein a weight ratio of the chain end functionalized polymer, the contrast material and the chemotherapeutic agent is 5~50:2.5~20:1~2, and
wherein the anti-cancer medicine is in a form of a nanoparticle having a micelle structure.

2. The polymeric anti-cancer medicine having a micelle structure according to claim 1, wherein the chain end functionalized polymer has a number-average molecular weight of 1,100 to 23,000.

3. The polymeric anti-cancer medicine having a micelle structure according to claim 1, wherein a particle size of the polymeric anti-cancer medicine is 30 to 200 nm.

4. The polymeric anti-cancer medicine having a micelle structure according to claim 1, wherein the contrast material is selected from iron oxide, gadolinium, manganese, aluminum, silicon, barium, yttrium and rare earth elements.

5. The polymeric anti-cancer medicine having a micelle structure according to claim 1, wherein the contrast material is an iron oxide.

6. The polymeric anti-cancer medicine having a micelle structure according to claim 1, wherein the chemotherapeutic agent is doxorubicin, adriamycin, cisplatin, taxol, 5-fluorouracil or pharmaceutically acceptable salts thereof.

7. The polymeric anti-cancer medicine having a micelle structure according to claim 1, wherein the chemotherapeutic agent is doxorubicin or pharmaceutically acceptable salts thereof.

8. The polymeric anti-cancer medicine having a micelle structure according to claim 1, wherein the chemotherapeutic agent is doxorubicin hydrochloride.

9. The polymeric anti-cancer medicine having a micelle structure according to claim 1, wherein the cancer is solid cancer.

10. The polymeric anti-cancer medicine having a micelle structure according to claim 1, wherein the cancer is primary cancer.

11. The polymeric anti-cancer medicine having a micelle structure according to claim 1, wherein the cancer is metastatic cancer.

12. A method of preparing a polymeric anti-cancer medicine having a micelle structure according to claim 1, comprising,
dissolving the chemotherapeutic agent in dimethylsulfoxide (DMSO) to prepare a DMSO solution of the drug;
adding triethylamine to the solution obtained;
dissolving the chain end functionalized polymer in the DMSO to prepare a DMSO solution of the polymer;
mixing the DMSO solution of the chemotherapeutic agent and the DMSO solution of the polymer;
adding the contrast material to the solution obtained; and
dialyzing and lyophilizing the solution obtained.

13. The method according to claim 12, wherein the chemotherapeutic agent is doxorubicin hydrochloride and the contrast material is an iron oxide, and in the dissolving the chemotherapeutic agent in DMSO, the doxorubicin hydrochloride is dissolved in the DMSO only.

* * * * *